US008852865B2

(12) United States Patent
Endress et al.

(10) Patent No.: US 8,852,865 B2
(45) Date of Patent: *Oct. 7, 2014

(54) METHOD AND SYSTEM FOR AUTOMATED IMAGE ANALYSIS IN CANCER CELLS

(71) Applicant: NeoDiagnostix Inc, Rockville, MD (US)

(72) Inventors: Gregory Anton Endress, Belchertown, MA (US); Madhvi Upender, Potomac, MD (US); Elizabeth Light, Gaithersburg, MD (US); Colyn Cain, Bethesda, MD (US)

(73) Assignee: NeoDiagnostix, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,432

(22) Filed: Nov. 1, 2013

(65) Prior Publication Data
US 2014/0135229 A1 May 15, 2014

Related U.S. Application Data

(63) Continuation of application No. 12/840,927, filed on Jul. 21, 2010, now Pat. No. 8,603,747.

(60) Provisional application No. 61/227,270, filed on Jul. 21, 2009.

(51) Int. Cl.
C12Q 1/68 (2006.01)
G06T 7/00 (2006.01)

(52) U.S. Cl.
CPC ..... *C12Q 1/6816* (2013.01); *G06T 2207/10056* (2013.01); *G06T 2207/10064* (2013.01); *G06T 2207/30024* (2013.01); *G06T 7/0012* (2013.01); *C12Q 1/6841* (2013.01); *G06T 2207/10024* (2013.01)
USPC ...................................................... 435/6.11

(58) Field of Classification Search
None
See application file for complete search history.

(56) References Cited

U.S. PATENT DOCUMENTS

| | | | |
|---|---|---|---|
| 5,919,624 | A | 7/1999 | Ried et al. |
| 8,409,808 | B2 | 4/2013 | Ried et al. |
| 8,603,746 | B2 | 12/2013 | Endress et al. |
| 8,603,747 | B2 | 12/2013 | Endress et al. |
| 2005/0026190 | A1 | 2/2005 | Sokolova et al. |
| 2006/0134622 | A1 | 6/2006 | Augustus et al. |
| 2007/0059697 | A1 | 3/2007 | Strovel et al. |
| 2008/0182253 | A1 | 7/2008 | Tafas et al. |
| 2008/0213769 | A1 | 9/2008 | Tafas et al. |
| 2009/0208965 | A1 | 8/2009 | Tafas et al. |
| 2009/0250629 | A1 | 10/2009 | Kim et al. |

FOREIGN PATENT DOCUMENTS

| | | |
|---|---|---|
| WO | WO 2005001137 A2 * | 1/2005 |
| WO | WO2004058050 | 2/2005 |
| WO | WO2006002378 | 7/2007 |
| WO | WO 2008070333 A2 * | 6/2008 |
| WO | WO2008070333 | 12/2008 |
| WO | WO2010011683 | 4/2010 |
| WO | 2011011527 | 1/2011 |

OTHER PUBLICATIONS

Cuzick et al., Vaccine, 2006, vol. 24S3, pp. S390-S397.*
Sopov, Int. J. of Cancer, 2004, vol. 112, pp. 33-43.*
Fitzpatrick, MA et al., Gyenecology Oncol 2006, 103:458-462.
Hopman, A.H. et al., J. Pathol. Dec. 2006; 210(4):412-9.
Heselmeyer-Haddad, K et al., Am J Pathol 2005, 166: 1229-1238.
Huang, FY et al., Cancer Genet Cytogenet 2005, 157:42-48.
Heselmeyer-Haddad, K et al., Am J Pathol 2003, 163:1406-1416.
Rao, PH et al., BMC Cancer 2004, 4:5-13.
Hesselmeyer et al., Genes, Chromosomes & Cancer 1997, 19:233-240.
Heselmeyer et al., PNAS 1996, 93:479-484.
Andersson et al., British Journal of Cancer 2006, 1-8.
Atkin, NB, 1997 Elsevier; 95:33-39.
Arias-Pulido, H. et al., 2002 Mol. Cancer; 1:3.
Rudlowski et al., Anatomic Pathology, 2003, 120, pp. 691-698.
Macville, M. et al., 1999 Cancer Res.; 59:141-50.
Lockwood, W. et al., Int. J. Cancer 2006; 120:436-443.
Takuma, Y. et al., 2004 Journal of Gastroenterology and Hepatology; 19:1300-1304.
Takahashi, S. et al., 2000 European Journal of Cancer; 36:496-502.
Toshikuni, N. et al., 2000 Br. J. Cancer; 82:833-837.
Zhang, A. et al., 2000 Cancer Res.; 60:6230-6235.
Zhang, A. et al., 2002 Genes Chromosomes Cancer; 34:269-75.
Huang, K.F. et al., J. Formos Med. Assoc. Nov. 2007 106(11):894-902.
Wilting et al., J. Pathol. 2006; 209:220-230.
Jee, K.J. et al. Mod Pathol. May 2001; 14(5):377-81.
Caraway, N.P. et al., Gynecol. Oncol. Jul. 2008: 110(1): 37-42. Epub Apr. 22, 2008.
Cao, Y. et al., Cancer Sci Jun. 2008: 99(6): 1092-1099.
Wolf, D.J. et al., (2007) Period Guidelines for Fluorescence In Situ Hybridization Testing.
Godoy et al., J of Cellular Physiology, 2006, 207, 614-27.
Grobhotz et al, Cancer Research, 1993, 53, pp. 4204-4211.

(Continued)

Primary Examiner — Michele K Joike
Assistant Examiner — Mindy G Brown
(74) Attorney, Agent, or Firm — Michele M. Wales; InHouse Patent Counsel, LLC

(57) ABSTRACT

A method of screening for the presence and/or extent of a pathology in a subject, the pathology characterized by an abnormal chromosomal component in a cell of the subject, comprising the steps of: contacting a biological sample comprising cell nuclei from said subject with, one or more distinguishable labeled probes directed to at least one chromosomal sequence that characterizes the abnormality under conditions that promote hybridization of the one or more probes to the at least one sequence, automatically obtaining a representation of the one or more distinguishable labels hybridized to the chromosomal sequences, automatically analyzing the distribution and intensity of binding of the one or more labels in the representation to determine the presence and/or extent of an abnormal chromosomal component; and automatically reporting results of the analysis; wherein the steps are carried out without intervention by a human.

60 Claims, 18 Drawing Sheets

(56) References Cited

OTHER PUBLICATIONS

Brown and Wahl, Cancer, 1993, 72, pp. 2979-2985.
Anju Zhang et al., Genetic Alterations in Cervical Carcinomas: Frequent Low-level Amplifications of Oncogenes are Associated with Human Papillom Virus Infection. Int. J. Cancer 101, 427-433 (2002).
Online Mendelian Inheritance in Man® (OMIM®), entry No. 123450, "Cri-du-Chat Syndrome", Creation date Apr. 14, 1994.
Mainardi, Orphanet Journal of Rare Diseases, 2006, vol. 1:33, pp. 1-9.
Cuzick et al., Vaccine, 2006, 24S3, pp. 90-97.
Santin et al., Virology, 2005, 331, pp. 269-291.
Ellis et al., Journal of Clinical Pathology, 2005, 58, pp. 710-714.

* cited by examiner

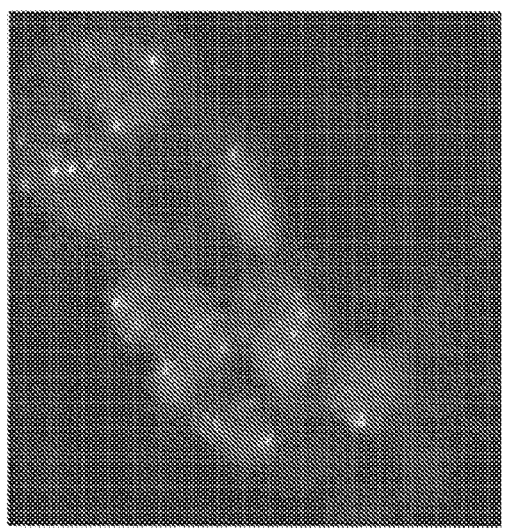
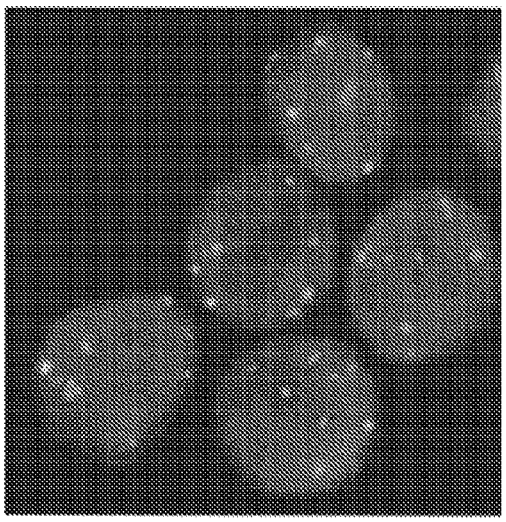
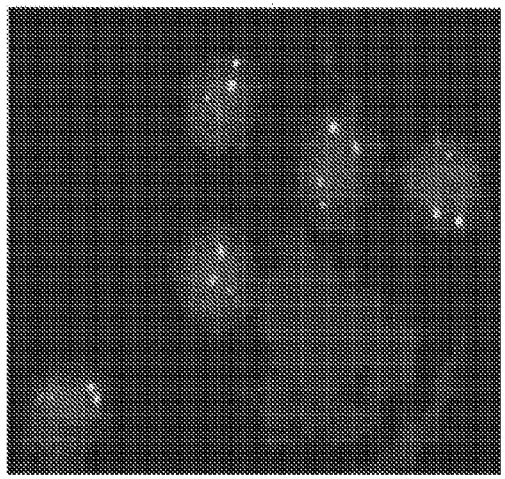
Figure 3

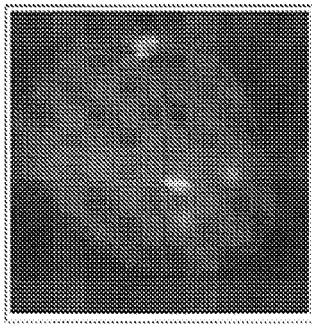

Interpretation: Evaluation of this specimen has revealed a normal copy number of the TERC gene. No amplification of the gene at 3q26 was detected and evaluation of the chromosome 7 centromere indicates a normal diploid cell. This does not rule out other abnormalities occurring at genetic loci other than those listed above. Detailed results of the analysis are summarized in the table above, along with a representative image of cells with normal copy of TERC.

Materials and Methods: Analysis for the Human Telomerase gene (TERC) was performed using Fluorescent In-Situ Hybridization (FISH) with a probe specific for the TERC gene on chromosome region 3q26. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

FIGURE 5

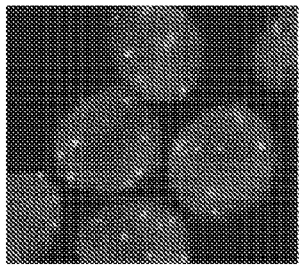

| | Total Cells | Abnormal Cells | Abnormal Cell Percentage |
|---|---|---|---|
| Number of Cells | 1030 | 18 | 1.85% |
| Test Result | | POSITIVE | |
| Reference Range | | | |
| Negative | <0.9% abnormal cells | | |
| Positive | ≥0.9% abnormal cells | | |

Interpretation: Evaluation of this specimen has revealed an abnormal copy number of the TERC gene. Detailed results of the analysis are summarized in the table above, along with a representative image of cells with abnormal copy of TERC.

Materials and Methods: Analysis for the Human Telomerase gene (TERC) was performed using Fluorescent In-Situ Hybridization (FISH) with a probe specific for the TERC gene on chromosome region 3q26. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

FIGURE 6

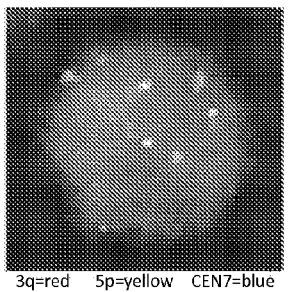

3q=red  5p=yellow  CEN7=blue

|  | Total Cells | Abnormal Cells | | | Abnormal Cell Percentage |
|---|---|---|---|---|---|
|  |  | 3q | 5p | 3q & 5p |  |
| Number of Cells | 1000 | 8 | 2 | 4 | 1.40% |
| Test Result | | POSITIVE | | | |
| Reference Range | | | | | |
| Negative | | | | | <1.0% abnormal cells |
| Positive | | | | | ≥1.0% abnormal cells |

Interpretation: Evaluation of this specimen has revealed an abnormal copy number of the chromosomal regions 3q26 and 5p15. Gain of chromosomal region 3q26 has been shown to be an early indicator of cervical dysplasia, while an increase in copy number at 5p15 is more often associated with more advanced stages of cervical carcinoma. Detailed results of the analysis are summarized in the table above, along with a representative image of cells with abnormal copy of region 3q26 and/or 5p15.

Materials and Methods: Analysis for the gene specific loci at chromosomal regions 3q26 and 5p15 was performed using Fluorescent In-Situ Hybridization (FISH) with a probe specific for the TERC gene on chromosome region 3q26 and the Cri du Chat locus at 5p15. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells.

FIGURE 7

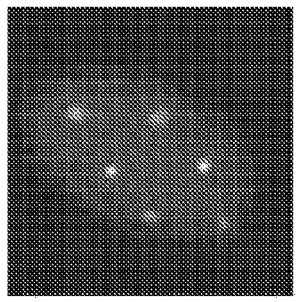

| | Total Cells | Abnormal Cells | | | Abnormal Cell Percentage |
|---|---|---|---|---|---|
| | | 3q | 5p | 3q & 5p | |
| Number of Cells | 1000 | 2 | 0 | 0 | 0.20% |
| Test Result | NEGATIVE | | | | |
| Reference Range | | | | | |
| Negative | | | | <1.0% abnormal cells | |
| Positive | | | | ≥1.0% abnormal cells | |

3q=red  5p=yellow  CEN7=blue

Interpretation: Evaluation of this specimen has revealed a normal copy number of chromosomal regions 3q26 and 5p15. In the number of cells analyzed, amplification of loci at 3q26 and 5p15 was not detected and evaluation of the chromosome 7 centromere indicates a normal diploid specimen. This does not rule out other abnormalities occurring at sites other than those listed above. Detailed results of the analysis are summarized in the table above, along with a representative image of cell(s) with normal copy of loci 3q26 and/or 5p15.

Materials and Methods: Analysis for the gene specific loci at chromosomal regions 3q26 and 5p15 was performed using Fluorescent In-Situ Hybridization (FISH) with a probe specific for the TERC gene on chromosome region 3q26 and the Cri du Chat locus at 5p15. In addition, a probe specific for chromosome 7 centromere was applied to assess DNA ploidy. Cervical cells were fixed to a slide and hybridized with these fluorescent probes. Analysis of the hybridization was performed to assess the presence of normal and abnormal cells

FIGURE 8

A
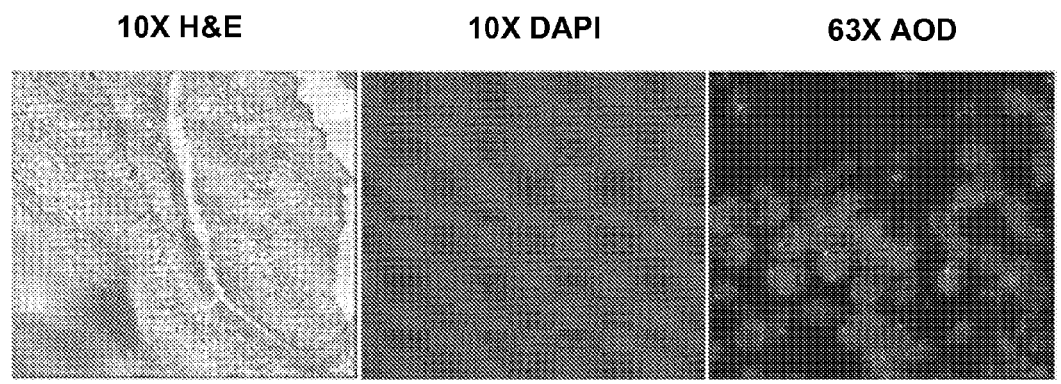
B
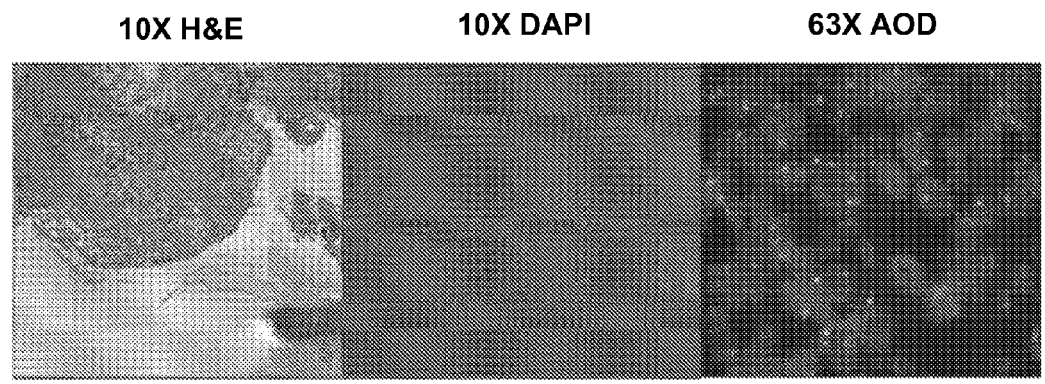
Figure 9

A
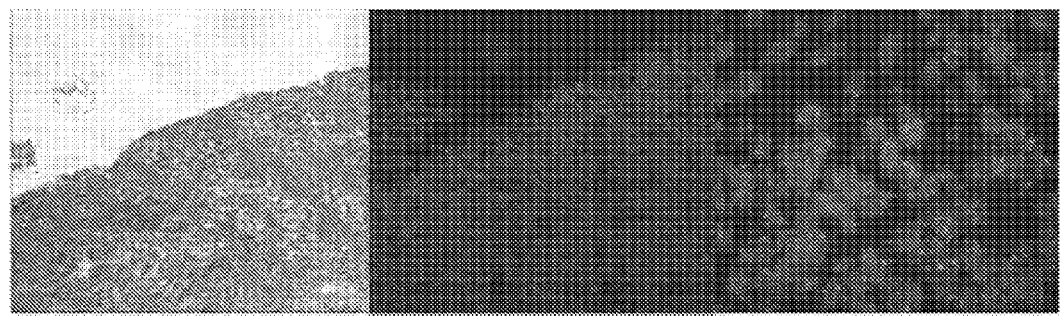
B
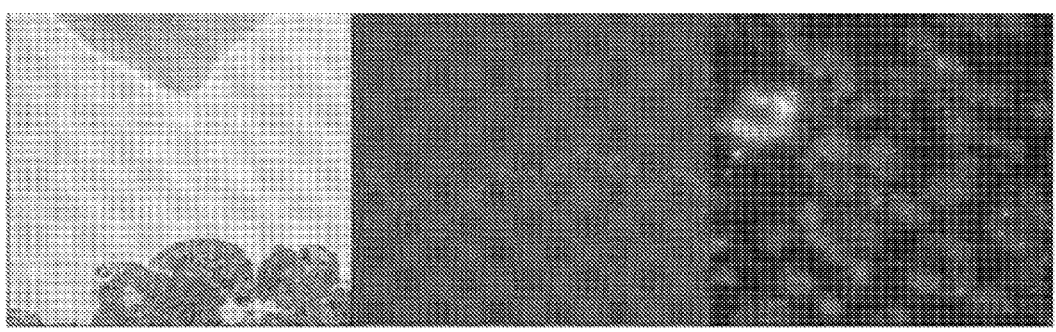
C
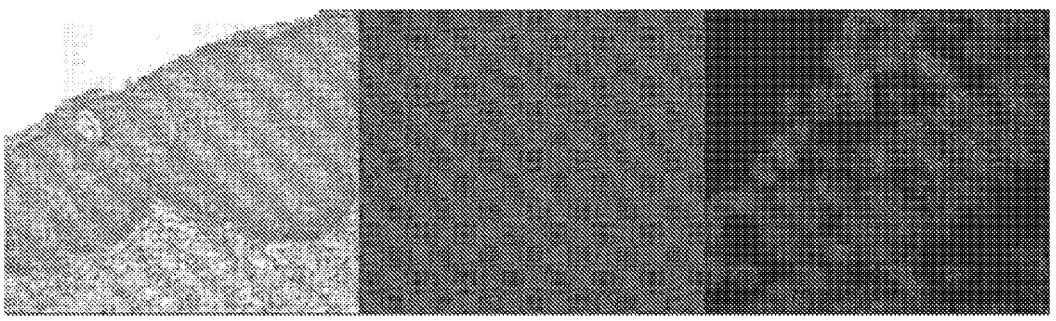
Figure 10

| GENE NAME | CHROMOSOME LOCATION | RefSeq NUMBER |
|---|---|---|
| PPM1L | 3q26.1 | NM_139245 |
| B3GALNT1 | 3q26.1 | NM_003781 |
| NMD3 | 3q26.1 | NM_015938 |
| C3orf57 | 3q26.1 | NM_001040100 |
| OTOL1 | 3q26.1 | NM_001080440 |
| SI | 3q26.1 | NM_001041 |
| SLITRK3 | 3q26.1 | NM_014926 |
| BCHE | 3q26.1 | NM_000055 |
| ZBBX | 3q26.1 | NM_024687 |
| WDR49 | 3q26.1 | NM_178824 |
| SERPINI2 | 3q26.1 | NM_006217 |
| PDCD10 | 3q26.1 | NM_145859 |
| SERPINI1 | 3q26.1 | NM_001122752 |
| GOLIM4 | 3q26.2 | NM_014498 |
| C3orf50 | 3q26.2 | NR_021485 |
| EVI1 | 3q26.2 | NM_001105077 |
| MDS1 | 3q26.2 | NM_004991 |
| TERC | 3q26.2 | NR_001566 |
| ARPM1 | 3q26.2 | NM_032487 |
| MYNN | 3q26.2 | NM_018657 |
| LRRC34 | 3q26.2 | NM_153353 |
| LRRIQ4 | 3q26.2 | NM_001080460 |
| LRRC31 | 3q26.2 | NM_024727 |
| SAMD7 | 3q26.2 | NM_182610 |
| LOC100128164 | 3q26.2 | NR_027622 |
| LOC100128164 | 3q26.2 | NR_024409 |
| SEC62 | 3q26.2 | MN_003262 |
| GPR160 | 3q26.2 | NM_014373 |
| PHC3 | 3q26.2 | NM_024947 |
| PRKCI | 3q26.2 | NM_002740 |
| SKIL | 3q26.2 | NM_005414 |

Figure 15A

| GENE NAME | CHROMOSOME LOCATION | RefSeq NUMBER |
|---|---|---|
| CLDN11 | 3q26.2 | NM_005602 |
| SLC7A14 | 3q26.2 | NM_020949 |
| RPL22L1 | 3q26.2 | NM_001099645 |
| EIF5A2 | 3q26.2 | NM_020390 |
| SLC2A2 | 3q26.2 | NM_000340 |
| TNIK | 3q26.2 | NM_001161560 |
| PLD1 | 3q26.31 | NM_002662 |
| FNDC3B | 3q26.31 | NM_022763 |
| GHSR | 3q26.31 | NM_198407 |
| TNFSF10 | 3q26.31 | NM_003810 |
| AADACL1 | 3q26.31 | NM_001146276 |
| ECT2 | 3q26.31 | NM_018098 |
| SPATA16 | 3q26.31 | NM_031955 |
| NLGN1 | 3q26.31 | NM_014932 |
| NAALADL2 | 3q26.31 | NM_207015 |
| TBL1XR1 | 3q26.32 | NM_024665 |
| KCNMB2 | 3q26.32 | NM_181361 |
| ZMAT3 | 3q26.32 | NM_152240 |
| PIK3CA | 3q26.32 | NM_006218 |
| KCNMB3 | 3q26.32 | NM_171830 |
| ZNF639 | 3q26.33 | NM_016331 |
| MFN1 | 3q26.33 | NM_033540 |
| GNB4 | 3q26.33 | NM_021629 |
| ACTL6A | 3q26.33 | NM_004301 |
| MRPL47 | 3q26.33 | NM_020409 |
| NDUFB5 | 3q26.33 | NM_002492 |
| USP13 | 3q26.33 | NM_003940 |
| PEX5L | 3q26.33 | NM_016559 |
| TTC14 | 3q26.33 | NM_001042601 |
| CCDC39 | 3q26.33 | NM_181426 |
| FXR1 | 3q26.33 | NM_001013438 |
| DNAJC19 | 3q26.33 | NM_145261 |
| SOX2OT | 3q26.33 | NR_004053 |
| SOX2 | 3q26.33 | NM_003106 |
| ATP11B | 3q26.33 | NM_014616 |
| DCUN1D1 | 3q26.33 | NM_020640 |

Figure 15B

| GENE NAME | CHROMOSOME LOCATION | RefSeq NUMBER |
|---|---|---|
| PLEKHG4B | 5p15.33 | NM_052909 |
| LOC389257 | 5p15.33 | NM_001080478 |
| CCDC127 | 5p15.33 | NM_145265 |
| SDHA | 5p15.33 | NM_004168 |
| PDCD6 | 5p15.33 | NM_013232 |
| AHRR | 5p15.33 | NM_020731 |
| C5orf55 | 5p15.33 | NM_138464 |
| EXOC3 | 5p15.33 | NM_007277 |
| LOC25845 | 5p15.33 | NR_024158 |
| SLC9A3 | 5p15.33 | NM_004174 |
| CEP72 | 5p15.33 | NM_018140 |
| TPPP | 5p15.33 | NM_007030 |
| ZDHHC11 | 5p15.33 | NM_024786 |
| BRD9 | 5p15.33 | NM_001009877 |
| TRIP13 | 5p15.33 | NM_004237 |
| NKD2 | 5p15.33 | NM_033120 |
| SLC12A7 | 5p15.33 | NM_006598 |
| SLC6A18 | 5p15.33 | NM_182632 |
| SLC6A19 | 5p15.33 | NM_001003841 |
| TERT | 5p15.33 | NM_198255 |
| CLPTM1L | 5p15.33 | NM_030782 |
| SLC6A3 | 5p15.33 | NM_001044 |
| LPCAT1 | 5p15.33 | NM_024830 |
| SDHAP3 | 5p15.33 | NR_003263 |
| LOC728613 | 5p15.33 | NR_003713 |
| MRPL36 | 5p15.33 | NM_032479 |
| NDUFS6 | 5p15.33 | NM_004553 |
| IRX4 | 5p15.33 | NM_016358 |
| IRX2 | 5p15.33 | NM_001134222 |
| C5orf38 | 5p15.33 | NM_178569 |
| IRX1 | 5p15.33 | NM_024337 |
| LOC340094 | 5p15.32 | NR_026994 |
| ADAMTS16 | 5p15.32 | NM_139056 |
| KIAA0947 | 5p15.32 | NM_015325 |
| FLJ33360 | 5p15.31 | NM_001001702 |
| MED10 | 5p15.31 | NM_032286 |

Figure 15C

| GENE NAME | CHROMOSOME LOCATION | RefSeq NUMBER |
|---|---|---|
| FLJ25076 | 5p15.31 | NM_001145161 |
| LOC255167 | 5p15.31 | NR_024424 |
| NSUN2 | 5p15.31 | NM_017755 |
| SRD5A1 | 5p15.31 | NM_001047 |
| POLS | 5p15.31 | NM_006999 |
| ADCY2 | 5p15.31 | NM_020546 |
| C5orf49 | 5p15.31 | NM_001089584 |
| FASTKD3 | 5p15.31 | NM_024091 |
| MTRR | 5p15.31 | NM_002454 |
| SEMA5A | 5p15.31 | NM_003966 |
| SNORD123 | 5p15.31 | NR_003689 |
| TAS2R1 | 5p15.31 | NM_019599 |
| LOC285692 | 5p15.31 - 5p15.2 | NR_027112 |
| FAM173B | 5p15.2 | NM_199133 |
| CCT5 | 5p15.2 | NM_012073 |
| CMBL | 5p15.2 | NM_138809 |
| MARCH6 | 5p15.2 | NM_005885 |
| ROPN1L | 5p15.2 | NM_031916 |
| DAP | 5p15.2 | NM_004394 |
| CTNND2 | 5p15.2 | NM_001332 |
| DNAH5 | 5p15.2 | NM_001369 |
| TRIO | 5p15.2 | NM_007118 |
| FAM105A | 5p15.2 | NM_019018 |
| FAM105B | 5p15.2 | NM_138348 |
| ANKH | 5p15.2 | NM_054027 |
| FBXL7 | 5p15.1 | NM_012304 |
| MARCH11 | 5p15.1 | NM_001102562 |
| ZNF622 | 5p15.1 | NM_033414 |
| FAM134B | 5p15.1 | NM_001034850 |
| MYO10 | 5p15.1 | NM_012334 |
| LOC285696 | 5p15.1 | NR_027253 |
| BASP1 | 5p15.1 | NM_006317 |

Figure 15D

METHOD AND SYSTEM FOR AUTOMATED IMAGE ANALYSIS IN CANCER CELLS

CROSS REFERENCE TO RELATED APPLICATIONS

This Application is a continuing application of and claims priority to U.S. Ser. No. 12/840,927 which was filed on Jul. 21, 2010, which is a non-provisional of and claims priority to U.S. Ser. No. 61/227,270 which was filed on Jul. 21, 2009. The entire contents of Ser. Nos. 12/506,985 and 61/227,270 are hereby incorporated by reference in their entirety.

FIELD

The invention relates, generally, to automated methods and system for detection of chromosomal abnormalities and automated image analysis in cells for the detection of cancer and dysplasias, more particularly, for the detection of cancers and dysplasias in cervical cells. U.S. Application 61/082,346 filed Jul. 21, 2008 is incorporated herewith in its entirety.

BACKGROUND

Cervical cancer is one of the most common and deadly cancers among women worldwide. If detected early, cervical cancer and precursor lesions can be treated effectively. A Pap test is the primary screen for cervical cancer and uses morphological analysis to identify suspicious cells. However, a single cytologic examination is relatively insensitive, poorly reproducible and frequently yields equivocal results. Approximately 6% of Papanicolaou (Pap) tests of 50 million performed annually in the United States are diagnosed as atypical squamous cells of undetermined significance (AS-CUS) and require follow-up testing, and approximately 5% of ASCUS patients have undetected cancer. Current guidelines for patients include follow-up Pap testing, testing for human papilloma virus (HPV) and/or colposcopy.

Current methods for Pap test also include liquid based cytological sampling and preparation of a monolayer of cells for analysis which have the additional benefit of use of the samples for HPV screening.

In addition, approximately 3% of Pap tests of the 50 million performed annually in the United States are diagnosed with low-grade squamous intraepithelial lesions (LSIL), Current guidelines for these patients recommend additional monitoring and/or colposcopy. Clinical studies show the majority of these patients are HPV+. There is significant risk for an ASCUS/HPV+ or LSIL patient to progress to more severe cervical disease and require surgical treatment within the two years following the initial test. The identification of these patients that will progress is impossible based on morphology and HPV infection.

Infection with HPV is associated with cervical cancer and many patients are tested for HPV after an ASCUS Pap test result or cotest for Pap/HPV in women whose cytology test is normal but are HPV positive. All HPV positive women are at risk for disease. The strength of sensitive HPV testing is that it provides extremely high negative predictive value; women who test negative are at low risk for developing cervical cancer. However, the positive predictive value of HPV testing is limited since only a small fraction of HPV positive early lesions progress to high-grade dysplasia and cancer. Thus, HPV detection, even in combination with cytomorphological evaluation, is a test with poor specificity.

Comparative genomic hybridization (CGH) is a molecular-cytogenetic method for the analysis of copy number changes (gains/losses) in the DNA content of a given subject's DNA and often performed on tumor cells, including cervical cancer. FISH methods can be used with CGH, array CGH, ELISA, or flow cytometry.

The implementation of cervical cancer screening programs has greatly reduced disease incidence and mortality in industrialized countries. However, a single cytological evaluation remains relatively insensitive, hence the need for frequent follow-up investigations. This is attributable to sampling or interpretation errors, and to the fact that some early lesions may not have acquired recognizable phenotypic alterations. Invasive cervical carcinomas develop through increasing stages of cervical dysplasia, to cervical intraepithelial neoplasias, categorized as CIN1, CIN2, CIN3, and to carcinoma in situ (CIS). While CIN3/CIS are considered bonafide precancerous lesions, current guidelines indicate surgical treatment for all CIN2 or more severe lesions. Only about 15% of all grades dysplastic lesions follow this path of progression. Pap and HPV tests are indirect methods for determining the presence of cervical dysplasia or cancer.

Manual methods are presently known to aid in the microscopic analysis of samples for determining increases or decreases in chromosomal copy number. By way of example, not limitation, nucleic acid probes can be labeled and directed to specific chromosomal structures; such probes are distinguishably labeled, with labels which fluoresce with different colors. Chromosomal structure may be elucidated, identified and analyzed using typical techniques of microscopic detection.

Fluorescent in situ hybridization (FISH) allows for visualization of genetic material in individual cells. FISH is particularly versatile because it can be performed on cells that can be actively or not actively dividing. FISH can be used in a variety of ways, including the use of locus specific probes to visualize a small portion of a gene, where the FISH probes only bind to the parts of the chromosomes to which they have a high degree of sequence similarity. To visualize the chromosomal region of interest, the FISH probe must be made to hybridize specifically to a target sequence, the probes can then be tagged directly with fluorophores or with targets for antibodies or with biotin.

Specifically, FISH involves the precise annealing of a single stranded fluorescently labeled DNA probe to complementary target sequences. The hybridization of the probe with the cellular DNA site is visible by direct detection using fluorescence microscopy. After the probes are made, an interphase or metaphase preparation of the chromosomes is made and is firmly attached to a substrate such as glass. After contacting the labeled probe with the slides comprising the prepared cells, the sample is washed to remove any probes not hybridized. The slide is then scanned via microscopy after DAPI counterstaining to image the chromosomal regions of interest.

Typical microscopic automation can provide for efficient and expedient biological sample analysis. Automatic microscopy can include, but is not limited to, robotic microscopic systems, automatic operation, automated slide scanning, automated stage, automated slide cassettes and handling systems, and computer software systems to facilitate detection and analysis of fluorescent signals.

Presently there are no non-manual i.e. automated, methods for the automatic microscopic analysis of chromosomal abnormalities present in cervical cells to provide for direct methods of determining the presence of cervical dysplasia and cancer. Therefore, there remains a continuing unmet need for automated microscopic methods for detecting chromosomal abnormalities for the diagnosis of cervical disease.

In yet another example of probes, ProVysion Multi-color Probe Set manufactured by Abbott Molecular is designed to detect and quantify chromosome 8, the lipoprotein lipase (LPL) gene located at 8p22, and the C-MYC gene located at the 8q24 region. Gain of 8q24 and 8p21-22 (LPL) and loss of heterozygosity are two genetic alterations that have been observed in abnormal samples. The ProVysion Multi-color Probe Set consists of three probes with three separate fluorophore labels. The multicolor probe set design is said to permit simultaneous analysis of the three genomic markers within a single cell, CEP® 8 probe labeled with Spectrum Aqua. LSI LPL labeled with Spectrum Orange, and LSI C-MYC labeled with Spectrum Green. The CEP 8 alpha satellite DNA probe hybridizes to the centromere region of chromosome 8 (8p11.1-q11.1) and provides a mechanism for the identification of copy number of chromosome 8. The manufacturer asserts that in a normal cell hybridized with the ProVysion Multi-color Probe Set, the expected pattern is the two orange, two green and two aqua (2O2G2A) signal pattern, while in an abnormal cell, combinations of copies of the three probe signals may be observed. The test kit indicates that copy numbers of more or less than two of any probe indicates chromosome or gene gain or loss, respectively. Less than two copies of the LSI LPL or multiple copies of the LSI C-MYC Probe relative to CEP 8 copy number indicates loss of the LPL region and gain of the C-MYC region, respectively, relative to the chromosome 8 copy number.

U.S. Patent Publication Nos. 2004/028107 and 2005/0026190 to Vysis. Inc. assert methods of using probes and probe sets for the detection of high grade dysplasia and carcinoma in cervical cells. The methods entail hybridizing one or more chromosomal probes to a biological sample and detecting the hybridization pattern of the chromosomal probes to determine whether the subject has high grade dysplasia or carcinoma. The methods encompass the use of a set of one or more probes demonstrating a vector value of about 60 or less wherein the vector value is calculated by Vector= $[(100-\text{specificity})^2+(100-\text{sensitivity})^2]^{1/2}$. The chromosomal probes may comprise probes for specific loci, such as 8q24, 3q26, Xp22, and CEP 15, or probes, for example, substantially complementary to full coding sequence for each of HPV-16, HPV-18, HPV-30. HPV-45, HPV-51, and HPV-58. The biological sample screened may be prescreened for the presence of a cell cycle protein, such as p16 or Cyclin E, or a cell proliferation marker, such as protein Ki67 or PCNA.

U.S. Patent Publication 2006/0063194 to Abbott Molecular also discloses probe sets and methods of using probes and probe sets for the detection of cancer, particularly lung cancer. Locus specific probes and chromosome enumeration probes are used in conjunction, and the hybridization pattern of the same used to determine whether the subject has lung cancer. Chromosomal compositions are specified, for example, a probe set for determining lung cancer may comprise a 5p15 locus specific probe, a 8q24 locus specific probe, a chromosome 6 enumeration probe and a 7p12 locus specific probe.

SUMMARY

One aspect of the present invention provides for an automated microscopic method for detecting chromosomal abnormalities, in a patient sample, in order to determine presence of cervical cell disease, including cervical cancer or cervical dysplasia comprising: contacting the patient sample which comprises cervical cells on a slide with at least two distinguishably labeled probes directed to a portion of a chromosomal region of the cervical cells; hybridizing a target nucleic acid region on chromosome 5p, and more specifically 5p15 in the cervical cells with a first said labeled nucleic acid probe; hybridizing a target nucleic acid region on the centromere of chromosome 7 (CEN7), as an aneuploidy probe, with a second said labeled nucleic acid probe; and automatically scanning the sample with a microscope to detect the formation of the hybridization complexes on chromosome 5p and on CEN7 and to generate an image after sufficient time and conditions to permit hybridization; automatically analyzing the image to characterize the chromosomal profile in the cells to generate a diagnosis; and automatically reporting the diagnosis to a user. In some aspects, the aneuploidy probe may also be centromere of chromosome 3 (CEN3).

One aspect of the present invention provides for an automated microscopic method for detecting chromosomal abnormalities, in a patient sample, in order to determine presence of cervical cell disease, including cervical cancer or cervical dysplasia comprising: contacting the patient sample which comprises cervical cells on a slide with at least two distinguishably labeled probes directed to a portion of a chromosomal region of the cervical cells; hybridizing a target nucleic acid region on chromosome 3q, and more specifically 3q26 in the cervical cells with a first said labeled nucleic acid probe; hybridizing a target nucleic acid region on the centromere of chromosome 7 (CEN7), as an aneuploidy probe, with a second said labeled nucleic acid probe; and automatically scanning the sample with a microscope to detect the formation of the hybridization complexes on chromosome 3q and on CEN7 and to generate an image after sufficient time and conditions to permit hybridization; automatically analyzing the image to characterize the chromosomal profile in the cells to generate a diagnosis; and automatically reporting the diagnosis to a user. In some aspects, the aneuploidy probe may also be centromere of chromosome 3 (CEN3).

In another aspect of the present invention, the first probe can be directed to a portion of the chromosome region 3q, and more specifically 3q26. In yet another aspect of the invention, a first nucleic acid probe targeted to a region of 5p, a second probe targeted to a region of 3q, and an aneuploidy probe to CEN7, or in the alternative CEN3, is provided. Each being differentially labeled such that the probes fluoresce with different colors and can each be uniquely identified after hybridization with a sample and subsequent imaging.

As 3q and 5p are specific to carcinogenesis, the aneuploidy probe permits us to measure carcinogenic processes in general. Also, genetic alterations have been identified in the early development of cervical cancer that can predict the patient's risk of disease progression. These aberrations include gross changes in DNA content (e.g. ploidy) and the amplification of both a portion of chromosome 3, specifically locus 3q26, that includes a gene TERC that encodes a subunit of the telomerase protein and a portion of chromosome 5, specifically 5p15, that includes a gene, TERT, that encodes another subunit of the telomerase protein, both of which are linked to cell immortality. Studies have demonstrated multicolor fluorescent DNA probes can detect abnormalities in both ploidy, and 3q and 5p copy number by fluorescence in situ hybridization (FISH) with greater sensitivity and specificity than other methods.

In yet another aspect, the aneuploidy probes, such as CEN7 described herein, can also be a locus specific probe on an arm near the centromere of chromosome 7 such as probes to 7p12.

Another aspect of the invention provides for a method of screening for the presence and/or extent of a pathology in a subject, the pathology characterized by an abnormal chromosomal component in a cell of the subject, comprising the steps of: contacting a biological sample comprising cell nuclei from the subject with, one or more distinguishably labeled probes directed to at least one chromosomal sequence that characterizes the abnormality under conditions that promote hybridization of the one or more probes to the at least one sequence, automatically obtaining a representation of the one or more distinguishable labels hybridized to the chromosomal sequences, automatically analyzing the distribution and intensity of binding of the one or more labels in the representation to determine the presence and/or extent of an abnormal chromosomal component; and automatically reporting results of the analysis; wherein the steps are carried out without intervention by a human.

Yet another aspect of the invention provides for method of screening for an abnormality related to a cancer, a high grade hyperplasia or a high grade dysplasia in a subject, comprising the steps of: obtaining a biological sample comprising nuclei from the subject; contacting the biological sample with a first probe bearing a first detectable label directed to a chromosomal sequence related to the abnormality under conditions that promote hybridization of the probes to targeted chromosomal loci; contacting the sample under the hybridizing conditions with at least one of a detectably labeled reference probe directed to a chromosomal locus known not to be abnormal and further contacting the sample with a nuclear reference stain; automatically finding areas in the sample having the reference stain and imaging the labels bound to the chromosomal sequences; automatically analyzing the label image for the distribution and intensity of hybridized labels; and automatically reporting results of the analysis; wherein the steps are performed without intervention by a human.

These and other aspects of some exemplary embodiments will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments without departing from the spirit thereof.

DESCRIPTION OF THE DRAWINGS

FIGS. 3 A, B and C illustrate the stages of cervical cancer progression as represented by amplification of 3q26 chromosomal copy number gain.

FIG. 5 is an illustration of negative results from a liquid-based cytology patient sample testing for abnormality in 3q alone.

FIG. 6 is an illustration of positive results from a liquid-based cytology patient sample testing for abnormalities in 3q alone.

FIG. 7 is an illustration of positive results from a liquid-based cytology patient sample testing for abnormalities in 3q and 5p.

FIG. 8 is an illustration of negative results from a liquid-based cytology patient sample testing for abnormalities in 3q and 5p.

FIGS. 9 A and B is an illustration of negative results from a patient's tissue biopsy sample testing for abnormalities in 3q alone. FIG. 8A is from a CIN1 tissue biopsy. FIG. 8B is from a CIN2 biopsy.

FIGS. 10 A, B, and C is an illustration of positive results from a patient's tissue biopsy sample testing for abnormalities in 3q alone. FIG. 9A is from a CIN1 tissue biopsy. FIG. 9B is from a CIN2 tissue biopsy. FIG. 9C is from a CIN3 tissue biopsy.

FIGS. 15 A, B, C, and D illustrate a listing of genes that can be targeted by specific probes of the invention to measure chromosomal abnormalities in cervical cells.

DETAILED DESCRIPTION

Figure 1:
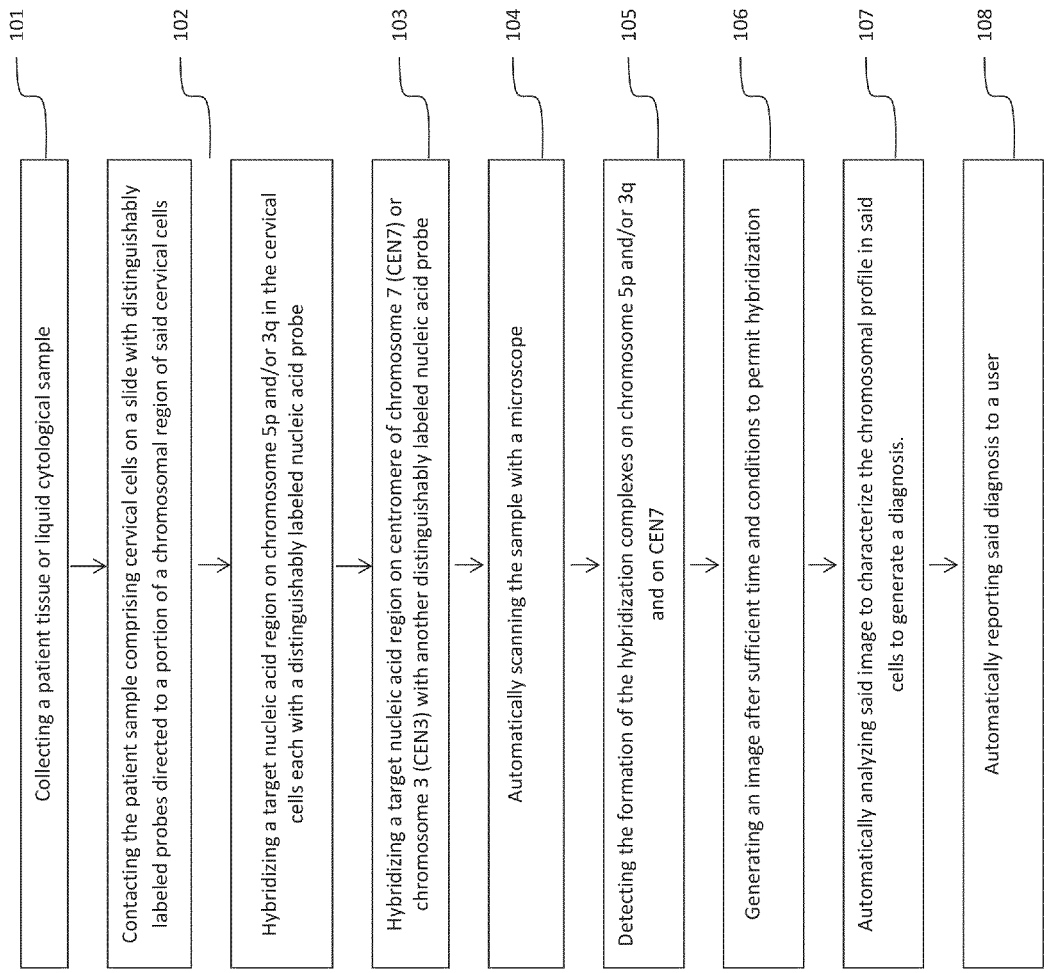
FIG. 1 is a flow diagram of an automated method for diagnosing cervical cell disease.
Figure 2:
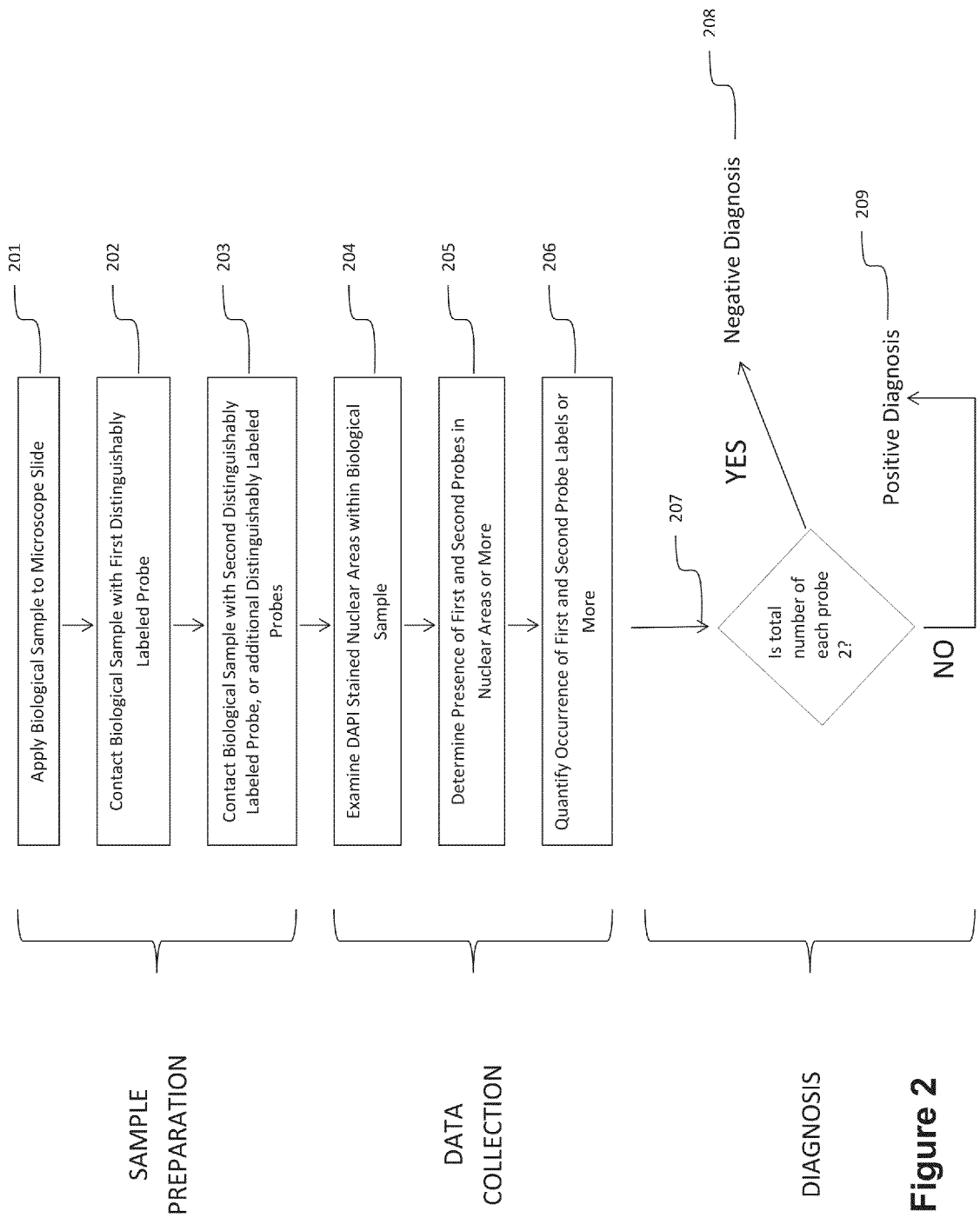
FIG. 2 is a flow diagram of another embodiment of the method of the invention.
Figure 4:
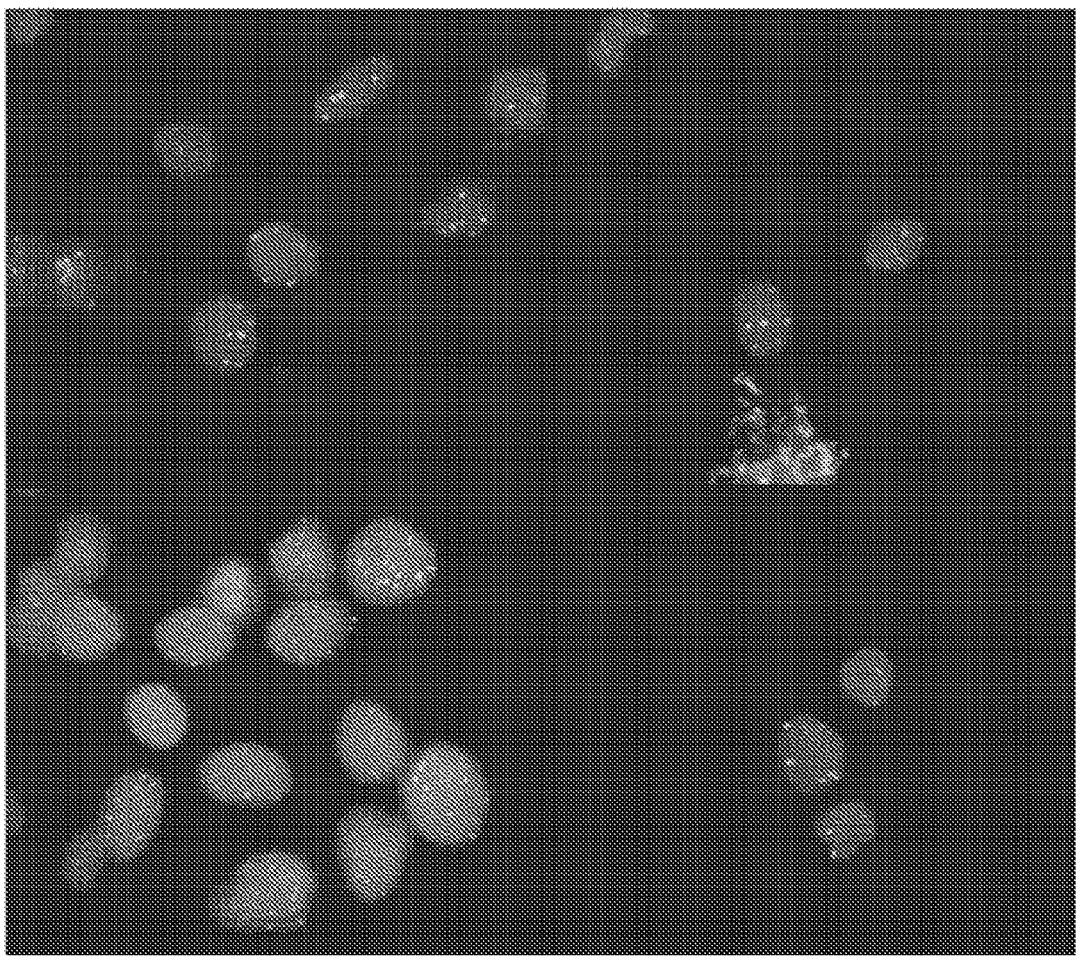
FIG. 4 illustrates the stages of cervical cancer progression as represented by amplification of 3q26 and 5p15 chromosomal copy number gain.
Figure 11:
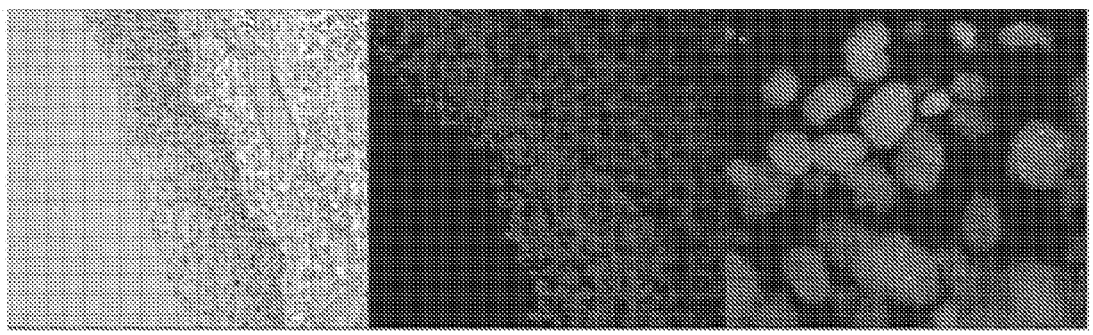
FIG. 11 is an illustration of results from a patient's tissue biopsy sample testing for abnormalities in 3q and 5p.
Figure 12:
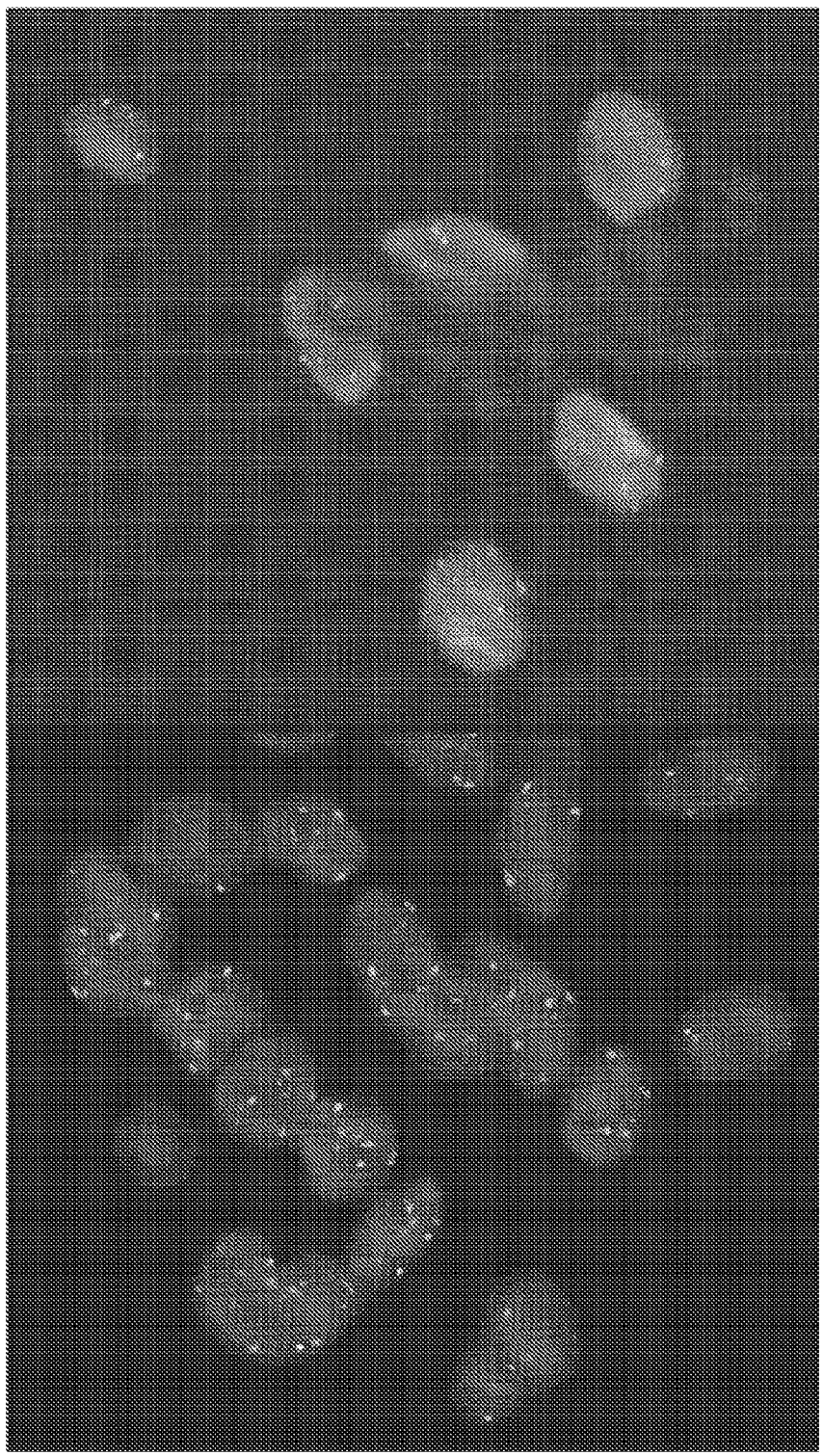
FIG. 12 is an illustration of a liquid-based cytology patient sample testing for abnormalities in 3q alone with tetraploid cells.
Figure 13:
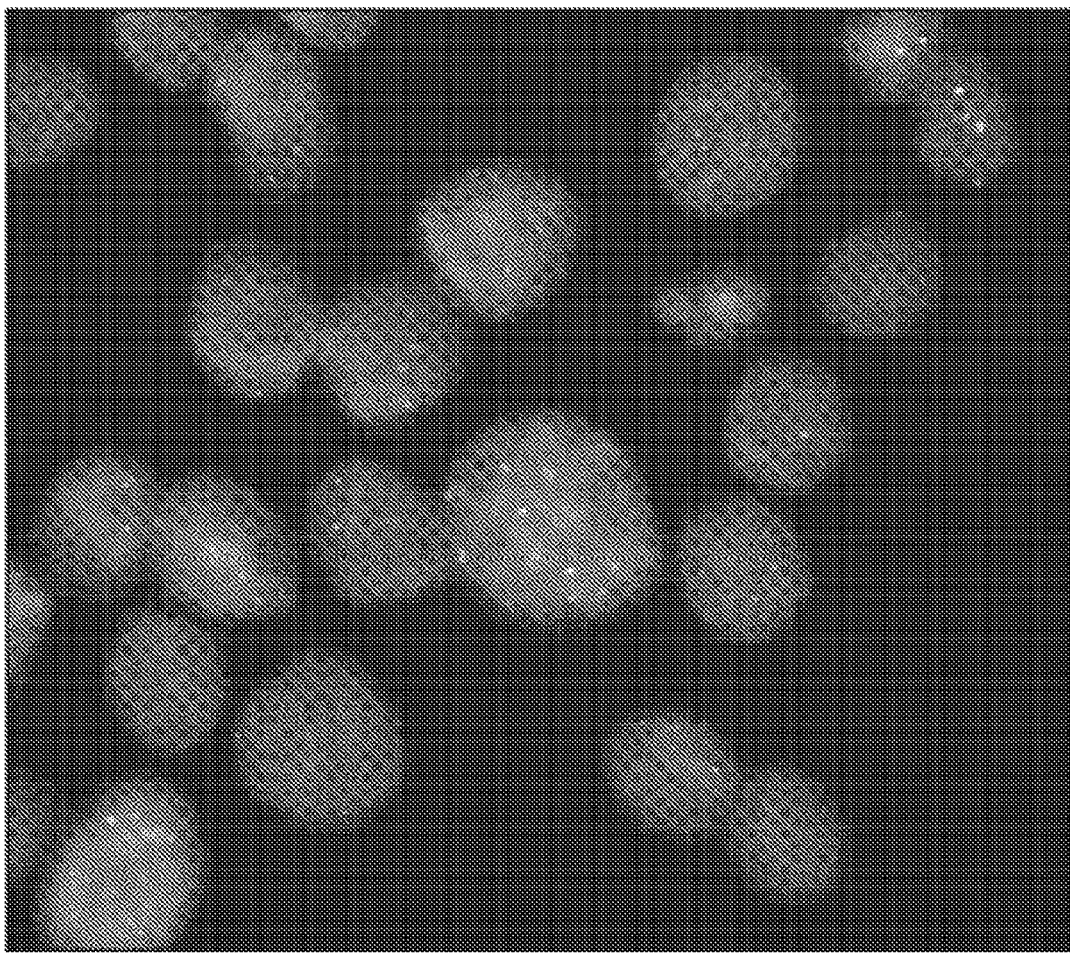
FIG. 13 is an illustration of a liquid-based cytology patient sample testing for abnormalities in 3q and 5p tetraploid cells.
Figure 14:
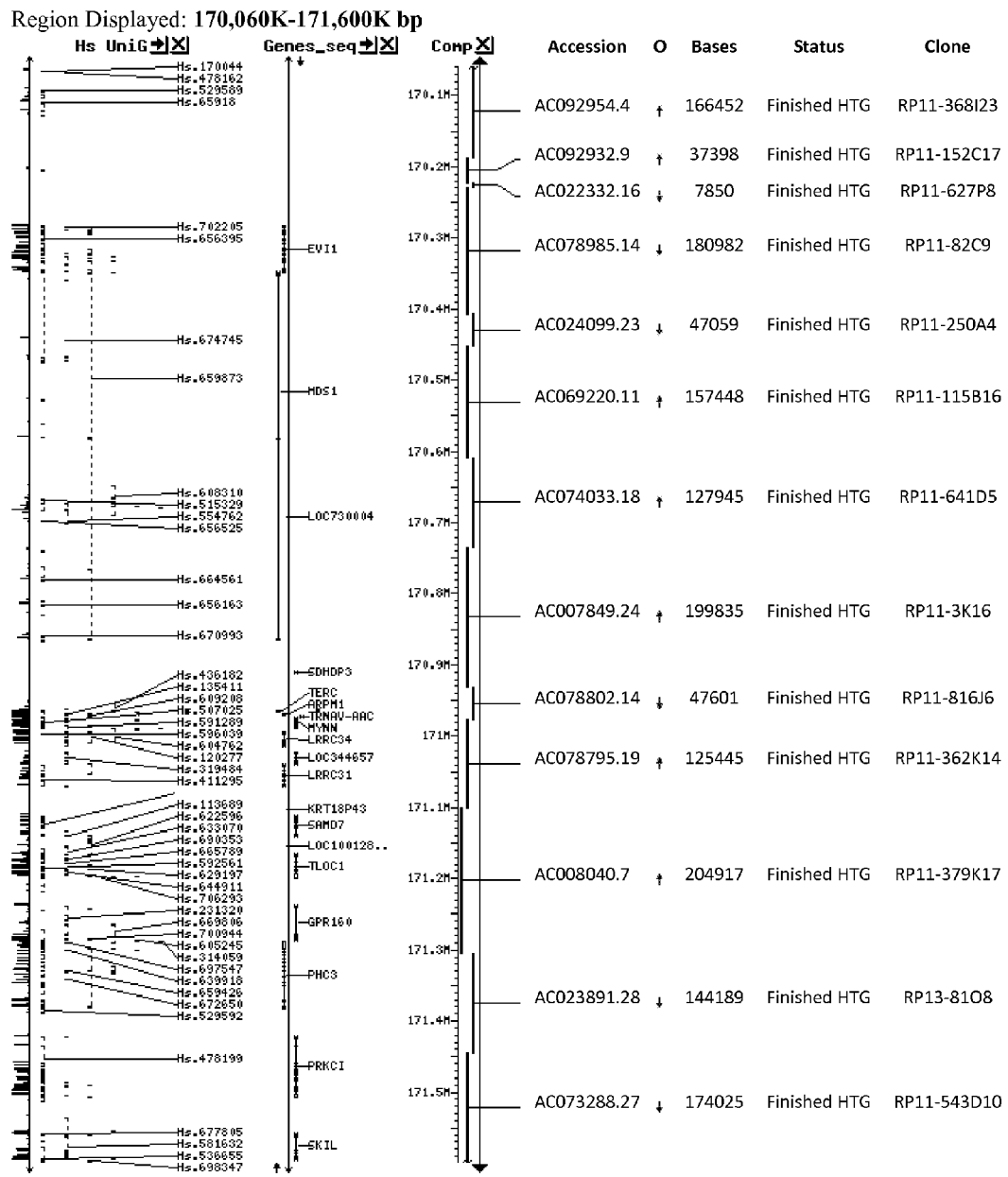
FIG. 14 illustrates genomic organization of chromosomal locus 3q26, including the gene position of TERC, among other genes, and BAC clones suitable for the production of labeled DNA probes.

The present invention is based on the identification of gain in copy number of chromosomal regions associated with cancer, and in particular cervical cancer.

The present invention provides for automated microscopic method for detecting chromosomal abnormalities in order to determine presence of cervical cell disease, including cervical cancer or cervical dysplasia, in a patient sample comprising: contacting the patient sample comprising cervical cells on a slide with at least two distinguishably labeled probes directed to a portion of a chromosomal region of the cervical cells; hybridizing a target nucleic acid region on chromosome 5p in the cervical cells with a first the labeled nucleic acid probe; hybridizing a target nucleic acid region on centromere of chromosome 7 (CEN7) with a second said labeled nucleic acid probe; and automatically scanning the sample with a microscope to detect the formation of the hybridization complexes on chromosome 5p and on CEN7 and to generate an image after sufficient time and conditions to permit hybridization; automatically analyzing the image to characterize the chromosomal profile in the cells to generate a diagnosis; and automatically reporting the diagnosis to a user.

The present invention provides for automated microscopic method for detecting chromosomal abnormalities in order to determine presence of cervical cell disease, including cervical cancer or cervical dysplasia, in a patient sample comprising: contacting the patient sample comprising cervical cells on a slide with at least two distinguishably labeled probes directed to a portion of a chromosomal region of the cervical cells; hybridizing a target nucleic acid region on chromosome 3q in the cervical cells with a first the labeled nucleic acid probe; hybridizing a target nucleic acid region on centromere of chromosome 7 (CEN7) with a second said labeled nucleic acid probe; and automatically scanning the sample with a microscope to detect the formation of the hybridization complexes on chromosome 3q and on CEN7 and to generate an image after sufficient time and conditions to permit hybridization; automatically analyzing the image to characterize the chromosomal profile in the cells to generate a diagnosis; and automatically reporting the diagnosis to a user.

As 3q and 5p are specific to carcinogenesis, the aneuploidy probe permits us to measure carcinogenic processes in general. These aberrations include gross changes in DNA content (e.g. ploidy) and the amplification of both a portion of chromosome 3, specifically locus 3q26, that includes a gene TERC that encodes a subunit of the telomerase protein and a portion of chromosome 5, specifically 5p15, that includes a gene, TERT, that encodes another subunit of the telomerase protein, both of which are linked to cell immortality. Studies have demonstrated multicolor fluorescent DNA probes can detect abnormalities in both ploidy, and 3q and 5p copy number by fluorescence in situ hybridization (FISH) with greater sensitivity and specificity than other methods. Therefore, in another embodiment of the invention, a first nucleic acid probe targeted to a region of 5p, a second probe targeted to a region of 3q, and an aneuploidy probe to CEN7, or in the alternative CEN3, is provided. Each being differentially labeled such that the probes fluoresce with different colors and can each be uniquely identified after hybridization with a sample and subsequent imaging.

In yet another embodiment, the aneuploidy probes, such as CEN7 described herein, can also be a locus specific probe on an arm near the centromere of chromosome 7 such as probes to 7p12.

It is yet another embodiment of the invention to provide for an automated microscope and system to perform each of the steps of the method disclosed herein. It is an embodiment of the invention whereby each of the step is carried out without manual intervention. It is also an embodiment of the invention, for the microscope to read a patient identified, e.g. barcode, on the slide for entry into a database prior to scanning so that the results of the method can be indexed according to each patient identifier.

In another embodiment, provided for is a method of screening for the presence and/or extent of a pathology in a subject, the pathology characterized by an abnormal chromosomal component in a cell of the subject, comprising the steps of: contacting a biological sample comprising cell nuclei from the subject with, one or more distinguishably labeled probes directed to at least one chromosomal sequence that characterizes the abnormality under conditions that promote hybridization of the one or more probes to the at least one sequence, automatically obtaining a representation of the one or more distinguishable labels hybridized to the chromosomal sequences, automatically analyzing the distribution and intensity of binding of the one or more labels in the representation to determine the presence and/or extent of an abnormal chromosomal component; and automatically reporting results of the analysis; wherein the steps are carried out without intervention by a human. A description of such methods can be found in US Patent Publication Numbers US 20090250629, US 20090208965, US 20080182253, and US 20080213769, each of which is hereby incorporated by reference in their entirety.

Yet another embodiment is a method of screening for an abnormality related to a cancer, a high grade hyperplasia or a high grade dysplasia in a subject, comprising the steps of: obtaining a biological sample comprising nuclei from the subject; contacting the biological sample with a first probe bearing a first detectable label directed to a chromosomal sequence related to the abnormality under conditions that promote hybridization of the probes to targeted chromosomal loci; contacting the sample under the hybridizing conditions with at least one of a detectably labeled reference probe directed to a chromosomal locus known not to be abnormal and further contacting the sample with a nuclear reference stain; automatically finding areas in the sample having the reference stain and imaging the labels bound to the chromosomal sequences; automatically analyzing the label image for the distribution and intensity of hybridized labels; and automatically reporting results of the analysis; wherein the steps are performed without intervention by a human. A description of such methods can be found in US Patent Publication Numbers US 20090250629, US 20090208965. US 20080182253, and US 20080213769, each of which is hereby incorporated by reference in their entirety.

Because cancer is a genetic disease, and genetic aberrations can be observed in diseased cells, the present method provides for automatic and efficient diagnosis of cervical disease by measuring such genetic abnormalities. The aberrations can be observed cytologically, by measuring genetic aberrations either as increase, hyperplasia, or decrease, hypoplasia, in copy number of gene regions collectively dysplasia. Also, certain chromosomal copy number differences are evident in cancer cells such that measurement of aneuploidy can be a diagnostic indicator of disease state in the cell, whether or not it can be observed cytologically. The methods discussed herein can directly identify abnormalities in the DNA of cervical cells using fluorescently labeled probes that bind to the aberrant regions in the chromosome. When greater than, or less than, the expected number of signals are observed, a cell sample can be diagnosed as diseased and cervical dysplasia can be diagnosed before it can be observed cytologically. Patients with these abnormalities can have a poor prognosis and can be at high risk to develop more advanced cervical disease. The methods disclosed herein can be performed subsequent to or in lieu of normal Pap, i.e. negative for intrathelial legions or malignancy (NILM), NILM/HPV+. HPV+, ASCUS/HPV+ or LSIL Pap tests, among other abnormal results from cytology testing, in order to provide more specific information about a patient's risk of disease progression.

As used herein. "copy number gain" or "amplification" means any chromosomal copy number greater than normal in a human pattern.

As used herein, "cervical cell disease" means any of the following: cervical carcinogenesis, Human Papilloma Virus (HPV) positive, Atypical Squamous Cells of Undetermined Significance (ASC-US), Low-grade Squamous lntraepithelial Lesion (LSIL), Atypical Squamous Cells, HSIL (ASC-H), Atypical Glandular Cells of Undetermined Significance (AGUS), High-grade Squamous lntraepithelial Lesion (HSIL), cervical dysplasia, pre-cancer, pre-malignant legion, cervical cancer, cervical adenocarcinoma, cervical squamous cell carcinoma, cervical intraepithelial neoplasia 1 (CIN1), cervical intraepithelial neoplasia (CIN2), cervical intraepithelial neoplasia 3 (CIN3), carcinoma in situ, invasive cervical carcinoma, and cytological or genetic abnormality of the cell and can be interchangeably used with cervical cancer or cervical dysplasia. Also, "disease." "cell disease," or "disease" as used herein includes but is not limited to any cytological or genetic abnormality of the cell.

"Human Papilloma Virus positive," "HPV+," or "HPV positive" as used herein means any HPV subtype identified by standard diagnostic HPV testing kits, such as those available from Qiagen of Maryland and Hologic of Massachusetts, including HPV subtypes 16, 18. The definition also includes the presence of HPV mRNA or the expression of HPV proteins, including E6, E7.

The present method provides direct identification of genetic abnormalities in morphologically normal cells and abnormal cells, as well as prognostic information about disease progression. In certain embodiments of the method, it may be used with squamous and glandular cervical cells or identify morphological characteristics that may be indicators of disease.

Copy Number Gains in Cervical Cancer

An increase in 3q copy number, in addition to integration of human papilloma virus (HPV) into the host genome, have been associated with the progression of CIN2 or CIN3 to cervical carcinoma and both appear to be important associated events in the progression of cervical dysplasia to invasive cancer. Hopman et al. J. Pathol. 2006 December: 210(4): 412-9. Higher staged tumors or those with lymph node metastasis had more chromosomal imbalances including gains of 3q; 1q; 8q; and losses of 11q; 3q; 6q and 2q. Gains of 3q1-q22 and 3q26-qter were more prevalent with lymph node metastasis. Huang. K. F. et al., J. Formos Med Assoc. 2007 November; 106(11): 894-902.

3q gains seen in invasive cervical carcinomas, specifically gain in the human telomerase gene (TERC), have been used in the development of FISH probe sets as a diagnostic tool in the detection of TERC gains in Pap smears. It has been suggested that TERC gains could predict progression from CIN1/CIN2 to CIN3 and invasive carcinoma. Heselmeyer-Haddad et al. Am Journal of Pathology 2005; 166:1229-1238.

5p is also a frequently observed structurally changed chromosome in carcinomas. Atkin, N. B 1997 Elsevier: 95: 33-39. Arias-Pulido, H. et al. 2002 Mol. Cancer; 1:3. Huang F. Y., et al. 2005 Cancer Gen. and Cyto., 157: 46-47. Macville M., et al. 1999 Cancer Res.; 59:141-50. Heselmeyer K. et al. 1997 Genes Chromosomes Cancer; 19: 233-40. Rao P. H. et al. 2004 BMC Cancer; 4:5. 5p gains are observed during progression to advanced stage carcinomas, and frequently involve whole arm amplifications. Heselmeyer K. et al. 1997 Genes Chromosomes Cancer: 19: 233-40.

Using carcinoma cell lines that showed 5p amplification, a minimal region of alteration at 5p13.33 has been defined, which encodes the human telomerase reverse transcriptase (hTERT) gene. Lockwood, W. et al. Int. J. Cancer 2006; 120: 436-443. Finally, an HPV integration site has also been mapped to 5p11-15. Lockwood, W. et al. Int. J. Cancer 2006; 120: 436-443. Telomerase activation is a component of cancer cell immortality Takuma, Y. et al. 2004 Journal of Gastroenterology and Hepatology: 19: 1300-1304. Takahashi S. et al. 2000 Eur. Jour. Of Cancer, 36: 496-502. Toshikuni, N. et al. 2000 Br. J. Cancer; 82; 833-837. hTERT has been identified as the catalytic subunit of telomerase. Takahashi S. et al. 2000 Eur. Jour. Of Cancer, 36: 496-502.

hTERT expression has been observed in several cancer cell lines, including cervical carcinomas, with certain cancer cell lines showing that hTERT expression is high in cancerous lesions but not non-cancerous tissues. Takahashi S. et al. 2000 Eur. Jour. Of Cancer, 36: 496-502. Although this differential expression was found in hepatocarcinomas rather than cervical carcinomas, the results suggest that hTERT expression occurred at an early stage of hepatocarcinogenesis. Takahashi S. et al. 2000 Eur. Jour. Of Cancer, 36: 496-502. Further, 5p hTERT gene amplification is closely correlated with increased hTERT mRNA expression in cervical cancers with HPV infection. Zhang A. et al. 2000 Cancer Res.; 60: 6230-6235. Zhang A. et al. 2002 Genes Chromosomes Cancer; 34: 269-75. 5p has been consistently identified as a chromosome that undergoes structural changes during various stages of carcinogenesis. The structural changes also appear to consistently affect the TERT gene encoded on 5p.

5p gain has been observed in invasive cervical carcinoma. Scotto, et al., Molecular Cancer 2008. When observed in samples in addition to observations of gain in 3q, specifically 3q26, it can be an indicator of increased progression of disease state from cervical dysplasia to invasive cervical carcinoma. Using a genomic probe for a region on 3q, specifically chromosome band 3q26, in combination with at least one aneuploidy probe. (eg. CEP3, CEN7), and a genomic probe for a region on 5p, especially 5p15, the copy number increases precede malignant conversion of cervical intraepithelial neoplasms to invasive carcinoma, and further accompany the transition from ASCUS or CIN1 to CIN2 or CIN3 and from CIN2 or CIN3 to carcinoma in situ to invasive cervical carcinoma. Moreover, the identification of gain in both 3q and 5p indicates an expedited transition from ASCUS or CIN1 to CIN2 or CIN3 and from CIN2 or CIN3 to carcinoma in situ to invasive cervical carcinoma.

The present methods provide for automated identification of possible cervical cell disease by comparing the copy number increase of the target chromosomes, for example, 5p, 3q or both together, as compared to normal. As used herein. "normal" means chromosomal diploidy in mammalian cells except when cells that are normally diploid are tetraphase and in the cell cycle and tetraploidy is observed. Chromosomal diploidy is measured by targeting a centromeric region, e.g. CEN3 or CEN7, with a probe. The automated methods can be used as a diagnostic and prognostic marker for cervical dysplasia in patients with ploidy abnormalities and/or increased 3q and/or increased $5_p$ copy numbers. Such methods for diagnosing cervical cell disease are fully disclosed in related applications U.S. Provisional Ser. No. 61/082,346; U.S. application Ser. No. 12/506,985; U.S. Provisional Ser. No. 61/227,270; U.S. Provisional Ser. No. 61/249,720; and U.S. application Ser. No. 10/540,311, each of which is incorporated by reference herein in its entirety, including any referenced cited therein.

The automated microscopy methods disclosed herein may further comprise, in addition to the use of distinguishably labeled probes for the detection of genetic amplification in chromosome 3q and 5p, the use of probes, distinguishably labeled for hybridization to regions of: 1q; 20q; 12q; 19q; 11q; 6q; 17p; 7; 8q, which is detected in late stage dysplasia; 9q; 16q; 2q; 9p; 10q; 18p and any combination thereof.

According to specific embodiments of the invention, amplification in the 3q26 locus and 5p15 locus band can be detected. In yet further specific embodiments of the invention, in addition to detection the 3q26 and 5p15 loci, amplification in the following chromosomal loci can be detected: 1q21-31; 20q12; 12q13-24; 19q13; 11q21; 7q11-22; 8q24 which is detected in late stage dysplasia; 9q33-34; 16q23; 2q32; 9p22; 10q21-24; 18p11 and any combination thereof.

The method can further comprise determining that the genomic amplification of chromosome 3q and/or chromosome 5p is not present in the sample. When compared to a state where aneuploidy is found and cervical cell disease is identified, the loss of chromosomal amplification can be indicative of regression of cell disease and possibly regression of disease. The method can include compiling individual patient data in a database whereby the results are studied for each sample. Subsequent test from the same patient are compared to prior recorded results to determine progression on regression of disease.

Generally, the automated method according to claim 1, 2 or 3, wherein said method analyzes a shift in patient condition from low grade to high grade cervical dysplasia or cancer or from high grade to low grade dysplasia; predisposition for or likelihood of developing a cervical cell disease; maintenance or regression of a patient condition; confirms or verifies the successful treatment of a cervical cell disease or monitors for recurrence and effectiveness of treatment; or quantifies the extent and/or severity of a cervical cell disease. The methods may also be used for assessing and monitoring late stage dysplasia comprising detecting genomic amplification in chromosomes 3q, as well as 5p and 8q, more specifically 8q24. Gain of 8q copy number and/or gain in 5p copy number in combination with gain in 3q, can indicate malignant conversion of cervical intraepithelial neoplasms to invasive carcinoma, and further accompany the transition from ASCUS/CIN1 to CIN2/CIN3 and from CIN2/CIN3 to carcinoma in situ to invasive cervical carcinoma and even to metastasis. Moreover, the identification of gain in both 3q and 5p indicates an expedited transition from ASCUS/CIN1 to CIN2/CIN3 and from CIN2/CIN3 to carcinoma in situ to invasive cervical carcinoma. Further, the method disclosed herein can be used to identify metastatic potential and metastasis of the disease.

In another embodiment, HPV infections may be involved in development of anal cancers because of the similar biology between cervical and anal carcinogenesis, including similar cell types and viral initiation, genomic abnormalities and copy number changes occur at 3q and 5p among other loci. Because anal cancer in patients approaches the rates of cervical cancer in women screening for HPV and/or bio-markers related to cervical cancer as disclosed herein can screen for anal cancer. It is therefore a further embodiment of the present invention to analyze anal cell specimens for 3q and 5p among the other chromosomal copy number changes to determine whether a patient may have anal disease. Therefore, these methods could be used on anal specimens and provide valuable clinical information regarding anal carcinogenesis.

Probes

A number of methods can be used to identify probes which hybridize specifically to the specific loci exemplified herein. For instance, probes can be generated by the random selection of clones from a chromosome specific library, and then mapped by digital imaging microscopy. This procedure is described in U.S. Pat. No. 5,472,842, herein incorporated by reference in its entirety. Various libraries spanning entire chromosomes are also available commercially from for instance Illumina Inc. Probes that hybridize specific chromosomal loci are available commercially from Abbot Molecular, Inc. (Des Plaines, Ill.).

Briefly, a genomic or chromosome specific DNA is digested with restriction enzymes or mechanically sheared to give DNA sequences of at least about 20 kb and more preferably about 40 kb to 300 kb. Techniques of partial sequence digestion are well known in the art. See, for example Perbal, A Practical Guide to Molecular Cloning, 2nd Ed., Wiley N.Y. (1998). The resulting sequences are ligated with a vector and introduced into the appropriate host. Exemplary vectors suitable for this purpose include cosmids, yeast artificial chromosomes (YACs), bacterial artificial chromosomes (BACs) and P1 phage. Various libraries spanning entire chromosomes are also available commercially.

Once a probe library is constructed, a subset of the probes is physically mapped on the selected chromosome. FISH and digital image analysis can be used to localize clones along the desired chromosome. Briefly, the clones are mapped by FISH to metaphase spreads from normal cells using e.g., FITC as the fluorophore. The chromosomes may be counterstained by a stain which stains DNA irrespective of base composition (e.g., DAPI or propidium iodide), to define the outlining of the chromosome. The stained metaphases are imaged in a fluorescence microscope with a polychromatic beam-splitter to avoid color-dependant image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere. This approach is described, for instance, in U.S. Pat. No. 5,472,842, herein incorporated by reference in its entirety.

Sequence information of the genes identified here permits the design of highly specific hybridization probes or amplification primers suitable for detection of target sequences from these genes. As noted above, the complete sequence of these genes or chromosomal regions can be identified by means known to those of skill in the art. For instance, oligonucleotide probes chosen to be complementary to a selected subsequence within the gene can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

Other probes used can be made by isolating DNA from BAC clones and labeling DNA. Chromosomal probes are typically about 50 to about $1\times10^5$ nucleotides in length. Longer probes typically comprise smaller fragments of about 100 to about 500 nucleotides in length. Probes that hybridize with centromeric DNA and locus-specific DNA are available commercially, for example, from Abbott Molecular, Inc. (Downers Grove, Ill.), Life Technologies, Inc. of California or Veridex of New Jersey. Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

In a preferred embodiment, probes of the present invention may be directed to at least a portion of TERC gene, at band 3q26.2, and TERT, TRIP13, at 5p15.3 or Cri du Chat locus at 5p15.2. Specifically, a probe to TERC at region 3q26 can be used labeled with spectrum gold and also a probe for 5p15 labeled with spectrum green. Such probes are commercially available from Abbot Molecular (Des Plaines, Ill.). However, the probes of the invention can include any gene on the 3q26 and 5p15 including, but not limited to, those referenced herein including those listed in FIG. 15 and any combination or portion of the genes on 3q26 or 5p1.5. In other embodiments, the target nucleic acid target comprises PIK3CA, PRCK1 or GLUT2.

In a specific embodiment, the detectable marker of the probe can emit a fluorescent signal or the probe may be chromogenic. The probes are hybridized using FISH as described herein. The present invention provides for an automated fluorescence microscopy platform that can be used to find out where the fluorescent probe binds to the chromosome. In instances where additional genetic material is required for testing, the genome may be amplified or detected by Polymerase Chain Reaction (PCR).

In another embodiment, the automated microscopy method as used herein comprises a procedure of performing FISH on liquid cytology specimens, such as SUREPATH® or THINPREP®, as well as tissue samples, or others as are known in the art, specimens for successful hybridization of DNA probes of the automated method described herein. SUREPATH® is available from Becton-Dickinson of Sparks, Md. THINPREP® is available from Hologic Laboratories of Bedford, Mass.

It is yet another aspect of the invention to use antibodies to separate squamous and glandular cells out of liquid-based cytology specimens prior to detecting genetic amplification in sample cells. The separation of cell types can improve detection of both squamous and glandular cancers and improve detection of cervical carcinomas which are rarely detected through traditional Pap testing but show 3q26 amplification, 5p15 amplification, or both. Glandular cells are lower in the tissue and present in the endocervical canal and abnormalities are likely to be missed in typical testing. If abnormalities are observed the likelihood of detecting and diagnosing cervical adenucarcinomas based on the analysis of glandular cells is increased as compared to testing of squamous cells or a mixed sample of squamous and glandular cells.

As used herein "label" or "labels" is any composition, e.g. probe, detectable by spectroscopic, photochemical, biochemical, immunochemical, or chemical means including but not limited to fluorescent dyes (e.g. fluorescein, rhodamine, Texas Red, etc., enzymes, electron dense reagents, magnetic labels, and the like). Labels which are not directly detected but are detected through the use of indirect label include biotin and dioxigenin as well as haptens and proteins for which labeled antisera or monoclonal antibodies are available. Methods of labeling nucleic acids and probes are well known to those of skill in the art. Preferred labels are those that are suitable for use in in situ hybridization. The nucleic acid probes may be detectably labeled prior to hybridization. Alternatively, a detectable label which binds to the hybridization product may be used. Such detectable labels include any material having a detectable physical or chemical property and are well developed in the field of immunoassays.

Typically, it is desirable to use multiple color, in a preferred embodiment three-color FISH methods for detecting chromosomal abnormalities in which three probes are utilized, each labeled by a different fluorescent dye. In the preferred embodiment, two test probes that hybridizes to the regions of interest are labeled with two different dyes and an aneuploidy probe that hybridizes to a different region is labeled with a third dye. More than three probes can be used so long as each is labeled with a unique dye. A nucleic acid probe that hybridizes to a stable region of the chromosome of interest such as the centromere, is preferred as an aneuploidy probe so that differences between efficiency of hybridization from sample to sample can be determined.

In a preferred embodiment comprising differentially labeled probes, the labeled probe panel may consist at least of a three-color, three-probe mixture of DNA probe sequences homologous to specific regions on chromosomes 3, 5 and 7; and/or other chromosome regions disclosed herein.

It is an embodiment of the system and method to be used in conjunction with specimens in liquid suspension, i.e. thin layer cytology specimen or thin layer suspension, that can be placed onto a microscope slide in an even, monolayer of cells, this includes liquid-base cytology specimens such as THINPREP® and SUREPATH® plus any fine-needle aspirate (FNA), sputum, or swab-based collection.

Cells recovered and isolated from specimens or samples collected from patients can be fixed on slides. Specimens can be retrieved using various techniques known in the art. In one embodiment specimens can be retrieved from THINPREP® and/or SUREPATH® samples, SUREPATH® is a Pap test used for the screening of cervical cancer. The THINPREP® Pap is also a liquid-based cytology method. A sample of the cervical cells is rinsed into a vial instead of a smear onto a slide thus preventing clumping of cells. The cells are separated in a laboratory to eliminate blood and mucus and the cells to be studied are then placed on a slide for studies to detect cancerous cells.

In addition to liquid or tissue sample from Pap, the method may also comprise analysis of tissue from cervical biopsies, punch biopsies, surgical procedures including LEEP, hysterectomy, CONE biopsy, ECC, CONE biopsy. The sample may be prepared from tissue or cells removed from the cervix, vagina, vulva or vaginal cuff, uterus, ovary or fallopian tube. The cells may be in metaphase or interphase.

In yet another embodiment, the nuclei can be isolated from a sample using methods known to those of skill in the art to/from single nuclei preparation from tissue samples. Wangsa et al., American Journal of Pathology, Vol. 175. No. 6, December 2009, incorporated in its entirety by reference herein.

Hybridization

In an embodiment, the regions disclosed here are identified using in situ hybridization. Generally, in situ hybridization comprises the following major steps: (1) fixation of tissue or biological structure to be analyzed; (2) pre-hybridization treatment of the biological structure to increase accessibility of target DNA, and to reduce nonspecific binding; (3) hybridization of the mixture of nucleic acids to the nucleic acid of the biological sample or tissue; (4) post-hybridization washes to remove nucleic acid fragments not bound in the hybridization and (5) detection of the hybridized nucleic acids. Hybridization protocols for the applications described herein are described in U.S. Pat. No. 6,277,563, incorporated herein by reference in its entirety.

From samples, the target DNA can be denatured to its single stranded form and subsequently allowed to hybridize with the probes of the method. Following hybridization, the unbound probe is removed by a series of washes, and the nuclei are counterstained with DAPI (4,6 diamidino-2-phenylindole), a DNA-specific stain. Hybridization of the DNA probes can be viewed using a fluorescence microscope equipped with appropriate excitation and emission filters allowing visualization of the aqua and gold fluorescent signals. Enumeration of CEN 7, 5p15 and 3q26 signals is conducted by microscopic examination of the nuclei.

The clinical test disclosed herein can use several biomarkers in combination for the early detection of cervical cancer and is important because current morphology based screening and detection methods have significant limitations. Identification of 3q26 and 5p15, among others, amplification and other cytogenetic abnormalities can more precisely and accurately identify patients at risk for developing cervical cancer and help them receive earlier treatment.

Image Analysis

The present invention provides for automatic image analysis and scoring of the methods disclosed via an automated microscope. The automated hybridization of the probe with the cellular DNA site is visible by direct detection using fluorescence microscopy as described herein. In a preferred embodiment, the probe panel consists of a 3-color, three-probe mixture of DNA probe sequences homologous to specific regions on chromosomes 3, 5, and 7. The probe mixture consists of a locus specific probe for chromosome 3q26, 5p15, and centromere of chromosome 7 (CEN7).

It is an embodiment of the present invention to provide for automated image analysis of the signal from the FISH probe. Microscopes can allow for automated capture of digital images of the field of view within the specimen/slide on the microscopy stage. Such manufacturers include Carl Zeiss, Leica. Nikon and Olympus. Also, the method provides for software platforms for automated image analysis such as microscope-software systems developed by such entities Applied Spectral Imaging of California, as Ikonisys of Connecticut, Metasystems of Massachusetts and Germany, Bioimagene of California, and Bioview of Massachusetts and Israel, among others. Such automated systems may apply to viewing 3q chromosomes alone or in combination with 5p abnormalities in the patient sample.

Cells recovered from specimens can be fixed on slides. The target DNA is denatured to its single stranded form and subsequently allowed to hybridize with the probes. Following hybridization, the unbound probe can be removed by a series of washes, and the nuclei are counterstained with DAPI (4,6 diamidino-2-phenylindole), a DNA-specific stain. Hybridization of the probes can be viewed using a fluorescence microscope equipped with appropriate excitation and emission filters allowing visualization of the three fluorescent signals. Enumeration of CEN7, 5p15 and 3q26 signals is conducted by automated microscopic examination of the nuclei.

The probe set and DAPI counterstain can be viewed on an automated epi-fluorescence microscope equipped with a 100-watt mercury lamp equipped with the following filters; DAPI, Spectrum Aqua (chromosome 7 centromere). Spectrum Green (locus on 5p15), and Spectrum Orange (locus on 3q26) or other labels and probes as are known in the art and disclosed herein. The automated microscopy with DAPI filter and a magnification of 10×, and 2×, 4× or 5× at the initial scan or subsequent passes, can automatically scan sample area of patient slide to determine cell quantity and quality. Analysis can begin in the upper left quadrant of the target area and scan fields with 63× oil, 40× or 20× or 63× or 100× or greater, objective from left to right and top to bottom without re-scanning the same areas. The system can count a total of about 1000 cells. The slides can be automatically located and unloaded onto the microscopy stage. After scanning, the computer software system automatically analyses the image and provides for automatic scoring of the cell counts and delivery of a report to a user.

Determination of chromosomal copy number in at least 800 cells, and preferably 1000 cells, is a preferred sampling of each clinical specimen. Less than 800 cells or more than 1000 cells can also be utilized in this system. The method and system overcome sampling variations and limitations of slide production methodology. The methods and system are consistent with methods recommended by professional medical organizations (ACMG) to determine the threshold between a specimen with and without chromosomal copy number changes. Wolf, D. J. et al. (2007) Period Guidelines for Fluorescence In Situ Hybridization Testing.

The automated method and system provides for at least 90% accuracy for positive specimens and identifies a patient with an increased risk of disease progression. The method and system can further provide for greater than 95% accuracy.

In situ hybridization is a technique that allows the visualization of specific nucleic acid sequences within a cellular preparation. Traditionally the visualization of probe signals has been performed manually by highly-trained personnel. Microscopes that can be used in the present method include, but are not limited to, those manufactured by Carl Zeiss, Leica, Nikon, and Olympus, which allow the user to capture digital images of the field of view within the specimen/slide on the microscopy stage. Software systems of the invention automatically acquire images from automatically loaded specimens/slide for high through put analysis. The automated systems include both a microscopy platform and the automated imaging software.

The type and source of the specimen to be analyzed directly impacts the analysis process and methodology. Each tissue type has its own biology and structure plus each cancer develops differently with different factors affecting the rate of carcinogenesis. In order to account for variation in cell biology, morphology and structure, the method can distinguish between epithelial and other cells and structures to avoid unwanted artifacts in the image. The software system of the invention can account for these different factors. Morphology can be automatically imaged where cells morphogenically suspicious for malignancy can be further analyzed for morphological abnormalities including, but not limited to, pyknosis, large nuclear size, irregular nuclear shape, and patchy DAPI staining. Therefore, the system can begin with cells that appear morphologically abnormal before counting normal cells. If few morphologically abnormal cells are present, cells which are the largest or have the largest detectable nuclei are scanned and analyzed. Overlapping cells that cannot be distinguished are not counted.

Further, another embodiment of the invention comprising identifying clusters or clumps of cells for morphological signals in abnormalities where said clusters can be indicative of more advanced cervical disease such as CIN2 or more severe disease.

Scoring and Analysis

The automated system then analyzes the image to automatically enumerate each probe signal within the DAPI-stained region and records the copy number of each probe identified. The software system continues its automated scoring of cells and chromosomal copy number within each cell until it obtains results of at least 800 cells in some embodiments 100.

200 or more cells. Once the 800 cell threshold is reached, the software can categorize each cell imaged and counted into a category based upon the copy number of each chromosome identified. By way of example, not limitation, normal cell with two copies of each probe 3q26, 5p15, and CEN7 would be placed into a 2,2,2 category. Abnormal cells would be identified by their probe signal patterns. For instance, a cell with two copies of the CEN7 probe, 5 copies of the 3q26 probe and 3 copies of the 5p15 probe can be placed in the 2,5,3 category. Once all of the imaged cells are categorized, the specimen can be evaluated relative to the positive/negative disease threshold. All cells identified as abnormal by the automated imaging system can be reviewed and verified manually by trained personnel before test results are communicated to a physician. The method and system further provides for automated verification. Specific cell threshold numbers can vary by specimen type and collection method. In addition, the software can be adapted to reflect biological, e.g. cell shape, cell size, DNA content of the nucleus, proximity of cells to each other, cell type, etc., or disease related differences, e.g. number of loci with abnormal number, the number of abnormalities at a locus within a single cell, relationship of an abnormality to survival or treatment response. This method and system can be used on a representative sampling of area covered by cells on the slide instead of the entire area, typically this is performed by imaging multiple fields of view or a path based on cellular density until the minimum imaged cell threshold is met.

In one embodiment, all cells identified as abnormal by the automated system are communicated electronically via methods known in the art to a physician or other user. Only a subset of the rank-ordered abnormal cells can be reviewed relative to the positive/negative test threshold as long as the clinical and disease significance is known for the subset. Typically the subset is the most abnormal about 25 or about 50 cells within the specimens, but other subsets can be identified and utilized depending on the specimen source, collection method, and disease.

Yet another embodiment can be used in conjunction with tissue-based specimens such as those from a biopsy or surgical procedure. In addition, this system and method can use a companion slide that is stained with hematoxylin and eosin stain (H&E) that comes from the same tissue-based specimen. This automated method screens the entire area covered by tissue-based specimen on the FISH prepared slide and utilizes the DAPI-stain to identify cellular nuclei. The system then enumerates each probe signal within the DAPI-stained region and records the copy number of each probe identified. The software system continues its automated scoring of cells and chromosomal copy number within each cell until the entire tissue-based specimen has been reviewed. The software then evaluates a sub-section of the slides that contains at least 25 nuclei as identified by the DAPI stain. The selection on the sub-section location is guided based upon disease indicators on the companion H&E slide. Typically, at least two sub-sections are selected for each specimen. The software then categorizes each cell imaged and counted into a category based upon the copy number of each chromosome identified.

In yet another embodiment, the system and method captures an image used alternatively for scoring by (1) identifying the image sample number and recording the image used (2) visualizing the signal colors separately (3) analyzing and recording the signal patterns for individual nuclei, selecting the appropriate nuclei based on the criteria described in preceding paragraph and (4) recording the signal numbers.

The software can automatically score data by: scanning the sample; recording and analyzing the image; calculating the number of any one of the signals, e.g. 3q, 5p, or CEN7, or other targeted regions as disclosed herein, and dividing by the total number of nuclei scored; recording that number in a Scoring Database. A result greater than 2 is recorded and reported as amplified for any given probe and is noted as abnormal and possible cervical cell disease. Images can be named by the specimen number and slide number and saved.

It is a preferred embodiment of the invention disclosed herein whereas all steps may be performed without human intervention.

EXAMPLES

Example 1

Methods and Specimen Selection for Automated Analysis and Scoring

A total of twenty-seven (27) specimens were identified within the tested population that had negative results for cytology, HPV and two-color method testing. In addition, these 27 specimens all had 1000 total cells counted in order to minimize variation within the analysis. The triple negative specimens were considered disease negative and, therefore, any abnormal cells identified by FISH would be considered 'false positives.' Once the number of 'false positive' cells is determined for the 27 specimens, the described BETAINV calculation can be used to determine the threshold between normal and abnormal specimens.

The results of FISH testing for the 27 triple negative specimens were reviewed to identify the total number of 'false positive' cells per specimen at each chromosomal loci. A specimen had 5 cells identified by FISH to be abnormal across both loci, 3q26 and 5p15, the greatest number of observed 'false positive' cells per specimen. This observation was used within the BETAINV calculation to determine the threshold between normal and abnormal specimens 95% confidence. The total number of cells entered into the equation was 1000. The BETAINV calculation returned a threshold value of 0.0104 (1.0%) or 10 cells out of 1000 counted cells. The threshold was also determined with 99% confidence and was equal to 0.0129 (1.3%) or 13 cells out of 1000.

In addition, the results of FISH testing for the 27 triple negative specimens were reviewed to identify the total number of 'false positive' cells per specimen at chromosomal locus 3q26 (TERC). The specimen had 3 cells identified by FISH to be abnormal 5p15, the greatest number of observed 'false positive' cells per specimen. This observation was used within the BETAINV calculation to determine the threshold between normal and abnormal specimens 95% confidence. The total number of cells entered into the equation was 1000 from ND10107B. The BETAINV calculation returned a threshold value of 0.0077 (0.7%) or 7 cells out of 1000 counted cells. The threshold was also determined with 99% confidence and was equal to 0.0104 (0.0104%) or 10 cells out of 1000.

In addition, the results of FISH testing for the 27 triple negative specimens were reviewed to identify the total number of 'false positive' cells per specimen at chromosomal locus 5p15 (Cri du Chat) and 3q26. The specimen had 3 cells identified by FISH to be abnormal 3q26, the greatest number of observed 'false positive' cells per specimen. This observation was used within the BETAINV calculation to determine the threshold between normal and abnormal specimens 95% confidence. The total number of cells entered into the equation was 1000. The BETAINV calculation returned a threshold value of 0.0104 (1.0%) or 10 cells out of 1000 counted cells. The threshold was also determined with 99% confidence and was equal to 0.0129 (1.3%) or 13 cells out of 1000.

Using the ACMG guidelines, the threshold between normal and abnormal specimens was determined for the automated analysis of the present method. With 95% confidence, the threshold was determined to be 10 cells out of 1000 cells or 1.0% abnormal cells per specimen. Therefore, any specimen with 1.0% or greater percentage of abnormal cells by FISH is abnormal and identifies a patient with a higher risk of progression. In these cases, a POSITIVE diagnostic test result can be issued. When a specimen is found to have less than 1.0% abnormal cells per specimen, a NEGATIVE diagnostic test report can be issued.

Example 2

FISH was performed on previously prepared thin layer, liquid-based cytology samples (THINPREP®, Cytye, Marlborough, Mass.). Slides were made from THINPREP® vials and then subject to a pretreatment protocol that includes protease digestion, formaldehyde fixation, washing, and dehydration. Hybridization was performed using a two-color multi-target interphase FISH probe kit (Abbot Molecular). The kit included directly labeled probes to CEN7-aqua and to the locus of 3q26 (3q-orange) and to the locus of 5p15 (5p-green). The cells were analyzed using fluorescence microscopy.

Samples had a minimum of 800 cells for analysis. Positive tests showed aneuploidy and (1) gains of either 3q copy number or 5p copy number in 1.0% or more of the analyzed cells; (2) gains of only 3q copy number of 0.9% or more of the analyzed cells; or (3) gains of only 5p copy number in 0.7% or more of the analyzed cells. Negative tests showed normal ploidy and (1) less than 1.0% of analyzed cells with an increase in both 3q copy number and 5p copy number; (2) gains of only 3q copy number in less than 0.9% of the analyzed cells; or (3) gains of only 5p copy number in less than 0.7% of the analyzed cells. Samples with ploidy abnormalities and/or increased 3q copy number were determined to have a poor prognosis and risk to develop more advanced cervical disease.

Results can be a diagnostic and prognostic marker for cervical dysplasia. Samples with ploidy abnormalities and/or increased 3q copy number and 5p copy number were determined to have a poor prognosis and risk to develop more advanced cervical disease.

Example 3

Evaluation of FIG. 7 this specimen has revealed an abnormal copy number of the TERC gene on 3q26 and the Cri du Chat locus 5p15. Of 1000 cells analyzed. 986 cells were normal while 8 were found abnormal for extra copies of TERC (3q). 2 were found abnormal for extra copies of Cri du Chat (5p), and 4 were found abnormal for extra copies of TERC and Cri du Chat (3q and 5p) for an abnormal cell percentage of 1.40%.

Example 4

Evaluation of FIG. 8 this specimen has revealed a normal copy number of the TERC gene on 3q26 and the Cri du Chat locus on 5p15. Of 1000 cells analyzed, 998 cells were normal while 2 were found abnormal for extra copies of TERC (3q), 0 were found abnormal for extra copies of Cri du Chat (5p), and 0 were found abnormal for extra copies of TERC and Cri du Chat (3q and 5p) for an abnormal cell percentage of 0.20%.

Example 5

Analysis for the Human Telomerase gene (TERC), 3q26, was performed using Fluorescent In-Situ Hybridization (FISH) with a probe specific for the TERC gene on chromosome region 3q26. In addition, a probe specific for CEN7 was applied to assess DNA ploidy. Cervical cells were fixed to a slide and hybridized with these fluorescent probes. Analysis of the hybridization was performed to assess the presence of normal and abnormal cells.

Example 6

Evaluation of FIG. 6 this specimen has revealed an abnormal copy number of the TERC gene. Along with a representative image of cells with an abnormal copy number of TERC. Of 1030 cells analyzed, 1012 cells were normal while 18 were found abnormal for an abnormal cell percentage of 1.85%.

Example 7

Evaluation of FIG. 5 revealed a normal copy number of the TERC gene. No amplification of the gene at 3q26 was detected and evaluation of the chromosome 7 centromere indicates a normal diploid cell. This does not rule out other abnormalities occurring at sites other than those listed above. Along with a representative image of cells with a normal copy of TERC. Of 800 cells analyzed, 799 cells were normal while 1 was found abnormal for an abnormal cell percentage of 0.1%.

Example 8

Tissue FISH

FISH was performed on 4-micron thick tissue sections cut from formalin fixed paraffin-embedded (FFPE) tissue specimens. (FIGS. 8 and 9) Slides were subject to a pretreatment protocol that includes protease digestion, washing, and dehydration. Hybridization was performed using a two-color FISH probe set containing directly labeled probes to CEN7-aqua and to the locus of 3q26 (3q-orange) (Probes obtained from Abbott Molecular). The sections were counterstained with DAPI and the cells were analyzed using fluorescence microscopy.

A minimum of fifty cells per sample were analyzed for ploidy status. Samples were judged aneuploid if the ratio of 3q26 probe signal to nuclei within the selected cells was 2.0 or greater. Samples were judged to have normal ploidy if the ratio of 3q26 probe signals to nuclei within the selected cells was less than 2. Patients with ploidy abnormalities and/or increased 3q copy number were determined at risk for a poor prognosis and are at high risk to develop more advanced cervical disease.

Results can be a diagnostic and prognostic marker for cervical dysplasia. Samples with ploidy abnormalities and/or increased 3q copy number were determined at risk for poor prognosis and to develop more advanced cervical disease.

Example 9

FISH was performed on 4-micron thick tissue sections cut from formalin fixed paraffin-embedded (FFPE) tissue specimens. (FIG. 10) Slides were subject to a pretreatment protocol that includes protease digestion, washing, and dehydration. Hybridization was performed using a three-color FISH probe set. The set included directly labeled probes to CEN7-aqua and to the locus of 3q26 (3q-orange) and to the locus of 5p15 (5p-green) (probes obtained from Abbott Molecular). The sections were counterstained with DAPI and the cells were analyzed using fluorescence microscopy. A minimum of fifty cells per sample were analyzed for ploidy status.

Samples were judged to have aneuploidy if (1) the ratio of 3q26 probe signal to nuclei within the selected cells was about 2.0 or greater, (2) the ratio of 5p15 probe signal to nuclei within the selected cells was about 2.0 or greater; (3) the ratio of 3q26 and 5p15 probe signals to nuclei within the selected cells was about 2.0 or greater. Samples were judged to have normal ploidy if the ratio of 3q26 or 5p15 or both 3q26 & 5p15 probe signals to nuclei within the selected cells was less than 2. Samples with ploidy abnormalities and/or increased 3q copy number were determined at risk for poor prognosis and at risk to develop more advanced cervical disease.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

Each of the applications and patents cited in this text, as well as each document or reference cited in each of the applications and patents (including during the prosecution of each issued patent: "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

Fitzpatrick, M A et al., Gynecology Oncol 2006, 103:458-462
Hopman, A H N et al., J Pathol 2006, 210:412-419
Heselmeyer-Haddad, K et al., Am J Pathol 2005, 166:1229-1238
Huang, F Y et al., Cancer Genet Cytogenet 2005, 157:42-48
Heselmeyer-Haddad, K et al., Am J Pathol 2003, 163:1406-1416
Rao, P H et al., BMC Cancer 2004, 4:5-13
Heselmeyer et al., Genes, Chromosomes, & Cancer, 1997, 19:233-240
Heselmeyer et al., PNAS, 1996, 93:479-484
Anderson et al., British Journal of Cancer, 2006, 1-8
Atkin, N. B., 1997 Elsevier; 95: 33-39
Arias-Pulido, H. et. al. 2002 Mol. Cancer; 1:3
Huang F. Y. et al. 2005 Cancer Gen. and Cyto., 157: 46-47
Macville M. et al. 1999 Cancer Res.; 59:141-50
Heselmeyer K. et al. 1997 Genes Chromosomes Cancer; 19: 233-40
Rao P. H., et al. 2004 BMC Cancer; 4:5
Lockwood W. et al. Int. J. Cancer 2006; 120: 436-443.
Takuma, Y. et al. 2004 Journal of Gastroenterology and Hepatology; 19: 1300-1304
Takahashi S. et al. 2000 Eur. Jour. Of Cancer, 36: 496-502
Toshikuni, N. et al. 2000 Br. J. Cancer; 82: 833-837
Zhang A. et al. 2000 Cancer Res.; 60: 6230-6235
Zhang A. et al. 2002 Genes Chromosomes Cancer; 34: 269-75
Huang, K. F. et al., J. Formos Med. Assoc. 2007 November; 106(11):894-902
Hopman. A. H. et al., J. Pathol. 2006 December; 210(4):412-9
Jee, K. J. et al., Mod Pathol. 2001 May; 14(5):377-81
Caraway, N. P. et al., Gynecol. Oncol. 2008 July; 110(1):37-42. Epub 2008 Apr. 22
Heselmeyer-Haddad, K. et al., American Journal of Pathology, 2005; 166:1229-1238
Cao, Y. et al., Cancer Sci 2008 June; 99(6): 1092-1099
Wolf, D. J. et al. (2007) Period Guidelines for Fluorescence In Situ Hybridization Testing.

What is claimed is:

1. An automated method for detecting chromosomal abnormalities in a plurality of cells in a cervical sample, said method comprising:
    a) contacting a cervical sample comprising cells with a plurality of distinguishably labeled nucleic acid sequences capable of hybridizing to chromosomal regions of said cells, wherein said plurality of distinguishably labeled nucleic acid sequences consists of:
        i) a first nucleic acid sequence to a target nucleic acid sequence on chromosome 3q;
        ii) a second nucleic acid sequence to a target nucleic acid sequence on chromosome 5p;
        iii) a third nucleic acid sequence to a target nucleic acid sequence on chromosome 1q;
    b) hybridizing the plurality of distinguishably labeled nucleic acid sequences;
    c) detecting a hybridization signal of the first, second and third nucleic acid sequences, wherein the hybridization signal of said first, second and third nucleic acid sequences is indicative of chromosomal copy number for 3q, 5p and 1q;
    d) scoring the chromosomal copy number for chromosomes 3q, 5p, and 1q; and
    e) reporting whether the sample contains chromosomal abnormalities wherein an increase in chromosomal copy number is indicative of chromosomal abnormalities in the cells.

2. The method of claim 1, wherein the scoring of the chromosomal copy number is performed by counting the cells having chromosomal abnormalities.

3. The method of claim 1, wherein the scoring of the chromosomal copy number is performed by counting hybridization signals.

4. The method according to claim 1, wherein each of the steps is performed by using an automated microscope.

5. The method according to claim 1, wherein the cells in said sample are deposited in a thin layer on a slide.

6. The method according to claim 1, wherein the cells in said sample are deposited on a slide, further comprising automatically loading and unloading said slides.

7. The method of claim 1, wherein the target nucleic acid sequence on chromosome 3q is at locus 3q26, 3q27, or 3q26.2.

8. The method of claim 1, wherein the target nucleic acid sequence on chromosome 3q is TERC, PIK3CA, PRCK1, or GLUT2.

9. The method of claim 1, wherein the target nucleic acid sequence on chromosome 5p is at locus 5p15, 5p15.3, or 5p15.2.

10. The method of claim 1, wherein the target nucleic acid sequence on chromosome 5p is TERT, TRIP13, or Cri du Chat locus at 5p15.2.

11. The method of claim 1, wherein the target nucleic acid sequence on chromosome 1q is at locus 1q21-31.

12. The method according to claim 1, wherein the method further comprises hybridizing at least one additional nucleic acid sequence to a target nucleic acid sequence on chromosome 20q, 12q, 19q, 11q, 6q, 17p, 7, 8q, 9q, 16q, 2q, 9p, 10q, or 18p.

13. The method according to claim 1, wherein the method further comprises hybridizing at least one additional nucleic acid sequence to a target nucleic acid sequence on chromosome 20q12, 12q13-24, 19q13, 11q21, 7q11-22, 8q24, 9q33-34, 16q23, 2q32, 9p22, 10q21-24, or 18p11.

14. The method according to claim 1, wherein the method further comprises hybridizing a nucleic acid sequence that binds to CENT or CEN3.

15. The method of claim 1, wherein the hybridization is detected by FISH, CISH, PCR, ELISA, CGH, Array CGH or flow cytometry.

16. An automated method for detecting chromosomal abnormalities in a plurality of cells in a cervical sample, said method comprising:
   a) contacting a cervical sample comprising cells with a plurality of distinguishably labeled nucleic acid sequences capable of hybridizing to chromosomal regions of said cells, wherein said plurality of distinguishably labeled nucleic acid sequences consists of:
      i) a first nucleic acid sequence to a target nucleic acid sequence on chromosome 3q;
      ii) a second nucleic acid sequence to a target nucleic acid sequence on chromosome 5p;
      iii) a third nucleic acid sequence to a target nucleic acid sequence on chromosome 20q;
   b) hybridizing the plurality of distinguishably labeled nucleic acid sequences;
   c) detecting a hybridization signal of the first, second and third nucleic acid sequences, wherein the hybridization signal of said first, second and third nucleic acid sequences is indicative of chromosomal copy number for 3q, 5p and 20q;
   d) scoring the chromosomal copy number for chromosomes 3q, 5p, and 20q; and
   e) reporting whether the sample contains chromosomal abnormalities wherein an increase in chromosomal copy number is indicative of chromosomal abnormalities in the cells.

17. The method of claim 16, wherein the scoring of the chromosomal copy number is performed by counting the cells having chromosomal abnormalities.

18. The method of claim 16, wherein the scoring of the chromosomal copy number is performed by counting hybridization signals.

19. The method according to claim 16, wherein each of the steps is performed by using an automated microscope.

20. The method according to claim 16, wherein the cells in said sample are deposited in a thin layer on a slide.

21. The method according to claim 16, wherein the cells in said sample are deposited on a slide, further comprising automatically loading and unloading said slides.

22. The method of claim 16, wherein the target nucleic acid sequence on chromosome 3q is at locus 3q26, 3q27, or 3q26.2.

23. The method of claim 16, wherein the target nucleic acid sequence on chromosome 3q is TERC, PIK3CA, PRCK1, or GLUT2.

24. The method of claim 16, wherein the target nucleic acid sequence on chromosome 5p is at locus 5p15, 5p15.3, or 5p15.2.

25. The method of claim 16, wherein the target nucleic acid sequence on chromosome 5p is TERT, TRIP13, or Cri du Chat locus at 5p15.2.

26. The method of claim 16, wherein the target nucleic acid sequence on chromosome 20q is at locus 20q12.

27. The method according to claim 16, wherein the method further comprises hybridizing at least one additional nucleic acid sequence to a target nucleic acid sequence on chromosome 1q, 12q, 19q, 11q, 6q, 17p, 7, 8q, 9q, 16q, 2q, 9p, 10q, or 18p.

28. The method according to claim 16, wherein the method further comprises hybridizing at least one additional nucleic acid sequence to a target nucleic acid sequence on chromosome 1q21-31, 12q13-24, 19q13, 11q21, 7q11-22, 8q24, 9q33-34, 16q23, 2q32, 9p22, 10q21-24, or 18p11.

29. The method according to claim 16, wherein the method further comprises hybridizing a nucleic acid sequence that binds to CENT or CEN3.

30. The method of claim 16, wherein the hybridization is detected by FISH, CISH, PCR, ELISA, CGH, Array CGH or flow cytometry.

31. An automated method for detecting chromosomal abnormalities in a plurality of cells in a cervical sample, said method comprising:
   a) contacting a cervical sample comprising cells with a plurality of distinguishably labeled nucleic acid sequences capable of hybridizing to chromosomal regions of said cells, wherein said plurality of distinguishably labeled nucleic acid sequences comprises;
      i) a first nucleic acid sequence to a target nucleic acid sequence on chromosome 3q;
      ii) a second nucleic acid sequence to a target nucleic acid sequence on chromosome 5p;
      iii) a third nucleic acid sequence to a target nucleic acid sequence on chromosome 1q;
   b) hybridizing the plurality of distinguishably labeled nucleic acid sequences;
   c) detecting a hybridization signal of the first, second and third nucleic acid sequences, wherein the hybridization signal of said first, second and third nucleic acid sequences is indicative of chromosomal copy number for 3q, 5p and 1q;
   d) scoring the chromosomal copy number for chromosomes 3q, 5p, and 1q; and
   e) reporting whether the sample contains chromosomal abnormalities wherein a lack of chromosomal abnormalities exists when less than 1.0% of the analyzed cells contain a gain in chromosomal copy number.

32. The method of claim 31, wherein the scoring of the chromosomal copy number is performed by counting the cells having chromosomal abnormalities.

33. The method of claim 31, wherein the scoring of the chromosomal copy number is performed by counting hybridization signals.

34. The method according to claim 31, wherein each of the steps is performed by using an automated microscope.

35. The method according to claim 31, wherein the cells in said sample are deposited in a thin layer on a slide.

36. The method according to claim 31, wherein the cells in said sample are deposited on a slide, further comprising automatically loading and unloading said slides.

37. The method of claim 31, wherein the target nucleic acid sequence on chromosome 3q is at locus 3q26, 3q27, or 3q26.2.

38. The method of claim 31, wherein the target nucleic acid sequence on chromosome 3q is TERC, PIK3CA, PRCK1, or GLUT2.

39. The method of claim 31, wherein the target nucleic acid sequence on chromosome 5p is at locus 5p15, 5p15.3, or 5p15.2.

40. The method of claim 31, wherein the target nucleic acid sequence on chromosome 5p is TERT, TRIP13, or Cri du Chat locus at 5p15.2.

41. The method of claim 31, wherein the target nucleic acid sequence on chromosome 1q is at locus 1q21-31.

42. The method according to claim 31, wherein the method further comprises hybridizing at least one additional nucleic acid sequence to a target nucleic acid sequence on chromosome 20q, 12q, 19q, 11q, 6q, 17p, 7, 8q, 9q, 16q, 2q, 9p, 10q, or 18p.

43. The method according to claim 31, wherein the method further comprises hybridizing at least one additional nucleic acid sequence to a target nucleic acid sequence on chromosome 20q12, 12q13-24, 19q13, 11q21, 7q11-22, 8q24, 9q33-34, 16q23, 2q32, 9p22, 10q21-24, or 18p11.

44. The method according to claim 31, wherein the method further comprises hybridizing a nucleic acid sequence that binds to CENT or CEN3.

45. The method of claim 31, wherein the hybridization is detected by FISH, CISH, PCR, ELISA, CGH, Array CGH or flow cytometry.

46. An automated method for detecting chromosomal abnormalities in a plurality of cells in a cervical sample, said method comprises:
   a) contacting a cervical sample comprising cells with a plurality of distinguishably labeled nucleic acid sequences capable of hybridizing to chromosomal regions of said cells, wherein said plurality of distinguishably labeled nucleic acid sequences comprises;
      i) a first nucleic acid sequence to a target nucleic acid sequence on chromosome 3q;
      ii) a second nucleic acid sequence to a target nucleic acid sequence on chromosome 5p;
      iii) a third nucleic acid sequence to a target nucleic acid sequence on chromosome 20q;
   b) hybridizing the plurality of distinguishably labeled nucleic acid sequences;
   c) detecting a hybridization signal of the first, second and third nucleic acid sequences, wherein the hybridization signal of said first, second and third nucleic acid sequences is indicative of chromosomal copy number for 3q, 5p and 20q;
   d) scoring the chromosomal copy number for chromosomes 3q, 5p, and 20q; and
   e) reporting whether the sample contains chromosomal abnormalities wherein a lack of chromosomal abnormalities exists when less than 1.0% of the analyzed cells contain a gain in chromosomal copy number.

47. The method of claim 46, wherein the scoring of the chromosomal copy number is performed by counting the cells having chromosomal abnormalities.

48. The method of claim 46, wherein the scoring of the chromosomal copy number is performed by counting hybridization signals.

49. The method according to claim 46, wherein each of the steps is performed by using an automated microscope.

50. The method of claim 46, wherein the cells in said sample are deposited in a thin layer on a slide.

51. The method of claim 46, wherein the cells in said sample are deposited on a slide, further comprising automatically loading and unloading said slides.

52. The method of claim 46, wherein the target nucleic acid sequence on chromosome 3q is at locus 3q26, 3q27, or 3q26.2.

53. The method of claim 46, wherein the target nucleic acid sequence on chromosome 3q is TERC, PIK3CA, PRCK1, or GLUT2.

54. The method of claim 46, wherein the target nucleic acid sequence on chromosome 5p is at locus 5p15, 5p15.3, or 5p15.2.

55. The method of claim 46, wherein the target nucleic acid sequence on chromosome 5p is TERT, TRIP13, or Cri du Chat locus at 5p15.2.

56. The method of claim 46, wherein the target nucleic acid sequence on chromosome 20q is at locus 20q12.

57. The method according to claim 46, wherein the method further comprises hybridizing at least one additional nucleic acid sequence to a target nucleic acid sequence on chromosome 1q, 12q, 19q, 11q, 6q, 17p, 7, 8q, 9q, 16q, 2q, 9p, 10q, or 18p.

58. The method according to claim 46, wherein the method further comprises hybridizing at least one additional nucleic acid sequence to a target nucleic acid sequence on chromosome 1q21-31, 12q13-24, 19q13, 11q21, 7q11-22, 8q24, 9q33-34, 16q23, 2q32, 9p22, 10q21-24, or 18p11.

59. The method according to claim 46, wherein the method further comprises hybridizing a nucleic acid sequence that binds to CENT or CEN3.

60. The method of claim 46, wherein the hybridization is detected by FISH, CISH, PCR, ELISA, CGH, Array CGH or flow cytometry.

* * * * *

UNITED STATES PATENT AND TRADEMARK OFFICE
CERTIFICATE OF CORRECTION

| | | |
|---|---|---|
| PATENT NO. | : 8,852,865 B2 | Page 1 of 1 |
| APPLICATION NO. | : 14/069432 | |
| DATED | : October 7, 2014 | |
| INVENTOR(S) | : Gregory Anton Endress et al. | |

It is certified that error appears in the above-identified patent and that said Letters Patent is hereby corrected as shown below:

In the claims,

Column 24, line 8, column 25, line 11, and column 26, line 39, the word "CENT" should read --CEN7--.

Signed and Sealed this
Thirtieth Day of June, 2015

Michelle K. Lee
*Director of the United States Patent and Trademark Office*